(12) United States Patent
Dai et al.

(10) Patent No.: US 12,391,990 B2
(45) Date of Patent: Aug. 19, 2025

(54) DETERMINATION OF MAGNESIUM BODY CONCENTRATION

(71) Applicant: Vanderbilt University, Nashville, TN (US)

(72) Inventors: Qi Dai, Nashville, TN (US); Chang Yu, Nashville, TN (US); Martha Shrubsole, Nashville, TN (US); Xiangzhu Zhu, Nashville, TN (US); Douglas Seidner, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 885 days.

(21) Appl. No.: 17/621,996

(22) PCT Filed: Jun. 24, 2020

(86) PCT No.: PCT/US2020/039421
§ 371 (c)(1),
(2) Date: Dec. 22, 2021

(87) PCT Pub. No.: WO2020/264023
PCT Pub. Date: Dec. 30, 2020

(65) Prior Publication Data
US 2022/0267851 A1    Aug. 25, 2022

Related U.S. Application Data

(60) Provisional application No. 63/042,878, filed on Jun. 23, 2020, provisional application No. 62/865,544, filed on Jun. 24, 2019.

(51) Int. Cl.
*C12Q 1/6883* (2018.01)
*A61K 33/06* (2006.01)
*G16B 20/00* (2019.01)

(52) U.S. Cl.
CPC ............ *C12Q 1/6883* (2013.01); *A61K 33/06* (2013.01); *G16B 20/00* (2019.02); *C12Q 2600/154* (2013.01)

(58) Field of Classification Search
CPC ............ C12Q 1/6883; C12Q 2600/154; A61K 33/06; G16B 20/00
See application file for complete search history.

(56) References Cited

U.S. PATENT DOCUMENTS

| | | |
|---|---|---|
| 2016/0115525 A1 | 4/2016 | Ebenstein et al. |
| 2018/0094325 A1 | 4/2018 | Zhang et al. |
| 2019/0062817 A1 | 2/2019 | Rao et al. |

FOREIGN PATENT DOCUMENTS

WO   WO 2010/105724 A1   9/2010

OTHER PUBLICATIONS

Swaminathan, Magnesium Metabolism and its Disorders, Clinical Biochemist Reviews, 2003, 24, 47-66 (Year: 2003).*

(Continued)

*Primary Examiner* — Anne M. Gussow
*Assistant Examiner* — Allison E Schloop
(74) *Attorney, Agent, or Firm* — Stites & Harbison PLLC; Mandy Wilson Decker

(57) ABSTRACT

The presently-disclosed subject matter includes methods for detecting methylation biomarkers in a biological sample from a subject in need of assessment for magnesium deficiency status, methods of diagnosing magnesium deficiency, methods of diagnosing magnesium insufficiency, methods of treating magnesium deficiency, methods of diagnosing magnesium insufficiency, and methods of preventing or reducing a risk of developing a condition linked to magnesium deficiency.

13 Claims, 7 Drawing Sheets

(56) References Cited

OTHER PUBLICATIONS

Zhu et al., A Genome-Wide Methylation Study of Severe Vitamin D Deficiency in African American Adolescents, The Journal of Pediatrics, 2013, 162, 1004-1009.e1 (Year: 2013).*
Miyata et al., Bisulfite Sequencing for DNA Methylation Analysis of Primary Muscle Stem Cells, Methods in Molecular Biology, 2017 1668, 3-13 (Year: 2017).*
Yu et al., Tet-Assisted Bisulfite Sequencing (TAB-seq), Methods in Molecular Biology, 2018, 1708, 645-663 (Year: 2018).*
Nazor et al., Application of a low cost array-based technique—TAB-Array—for quantifying and mapping both 5mC and 5hmC at single base resolution in human pluripotent stem cells, Genomics, 2014, 104, 358-367 (Year: 2014).*
Nadler and Rude, Disorders of Magnesium Metabolism, Endocrinology and metabolism clinics of North America, 1995, 24, 623-641 (Year: 1995).*
Takaya et al., Magnesium deficiency in pregnant rats alters methylation of specific cytosines in the hepatic hydroxysteroid dehydrogenase-2 promoter of the offspring, Epigenetics, 2011, 6, 573-578 (Year: 2011).*
Barua et al. Lifestyle, pregnancy and epigenetic effects, Eplgenomics, Feb. 17, 2015 (Feb. 17, 2015), vol. 7, No. 1, pp. 85-102.
Tong GM, Rude RK. Magnesium deficiency in critical illness. J Intensive Care Med 2005;20:3-17.
Waters RS, Fernholz K, Bryden NA, Anderson RA. Intravenous magnesium sulfate with and without EDTA as a magnesium load test-is magnesium deficiency widespread? Biol Trace Elem Res 2008;124:243-250.
Dai Q, Shu XO, Deng X et al. Modifying effect of calcium/magnesium intake ratio and mortality: a population-based cohort study. BMJ Open 2013;3.
Saris NE, Mervaala E, Karppanen H, Khawaja JA, Lewenstam A. Magnesium. An update on physiological, clinical and analytical aspects. Clin Chim Acta 2000;294:1-26.
Hartwig A. Role of magnesium in genomic stability. Mutat Res 2001;475:113-121.
Lukaski HC, Nielsen FH. Dietary magnesium depletion affects metabolic responses during submaximal exercise in postmenopausal women. J Nutr 2002;132:930-935.
Blaschke K, Ebata KT, Karimi MM et al. Vitamin C induces Tet-dependent DNA demethylation and a blastocyst-like state in ES cells. Nature 2013;500:222-226.
Yin R, Mao SQ, Zhao B et al. Ascorbic acid enhances Tet-mediated 5-methylcytosine oxidation and promotes DNA demethylation in mammals. J Am Chem Soc 2013;135:10396-10403.
Flatman PW. Mechanisms of magnesium transport. Annu Rev Physiol 1991;53:259-271.
Baccarelli AA, Zheng Y, Zhang X et al. Air pollution exposure and lung function in highly exposed subjects in Beijing, China: a repeated-measure study. Part Fibre Toxicol 2014;11:51.
Hou L, Zhang X, Zheng Y et al. Altered methylation in tandem repeat element and elemental component levels in inhalable air particles. Environ Mol Mutagen 2014;55:256-265.
Hou L, Zhang X, Dioni L et al. Inhalable particulate matter and mitochondrial DNA copy number in highly exposed individuals in Beijing, China: a repeated-measure study. Part Fibre Toxicol 2013;10:17.
Dai Q, Shrubsole MJ, Ness RM et al. The relation of magnesium and calcium intakes and a genetic polymorphism in the magnesium transporter to colorectal neoplasia risk. Am J Clin Nutr 2007;86:743-751.
Dai Q, Sandler R, Barry E, Summers R, Grau M, Baron J. Calcium, magnesium, and colorectal cancer. Epidemiology 2012;23:504-505.

* cited by examiner (b) cg00430271 Mg deficiency (c) cg25731074 Mg not deficiency

DETERMINATION OF MAGNESIUM BODY CONCENTRATION

RELATED APPLICATIONS

This application claims priority from U.S. Provisional Application Ser. No. 62/865,544 filed Jun. 24, 2019 and 63/042,878 filed Jun. 23, 2020, the entire disclosures of which are incorporated herein by this reference.

GOVERNMENT INTEREST

This invention was made with government support under grant numbers CA149633 and CA202936 awarded by the National Institutes of Health. The government has certain rights in the invention.

TECHNICAL FIELD

The presently-disclosed subject matter generally relates to predicting and determining body magnesium status, treatment of magnesium deficiency, and treatment of conditions associated with magnesium deficiency.

INTRODUCTION

According to the US National Health and Nutrition Examination Survey (NHANES), 79% of US adults do not meet their Recommended Dietary Allowance (RDA) of $Mg^3$.

In the US and other Western populations at high risk of Mg deficiency, epidemiologic studies have linked low Mg intake to risks of colorectal neoplasia[4-6], insulin resistance[7-12] systemic inflammation[45;46] metabolic syndrome[6-18], type 2 diabetes (T2D)[11;19-23] and cardiovascular disease (CVD)[19;24-28] although not entirely consistent[26;27]. Conversely, in populations not at high risk of Mg deficiency, the opposite results have been reported[29]. In two large-scale Chinese cohort studies, high Mg intake was associated with an increased risk of total mortality (e.g. mortality due to total cancer, colorectal cancer (CRC), and CVD) among both men and women, particularly when Ca intake was below the median.

These findings are intriguing and suggest that the effects of high Mg intake may completely depend on the underlying Mg status. High-dose Mg supplementation or fortification may lead to problems in the subset of the US population who do not have Mg deficiency (i.e. at least 20%). Accordingly, it becomes critical to develop a personalized prevention strategy to minimize potential adverse effects (i.e. first identify individuals with Mg deficiency and target only those with Mg deficiency) for the prevention of CRC and other common diseases linked to Mg deficiency.

Serum Mg has been used to clinically diagnose Mg deficiency[1]. However, only about 0.3% of the total body Mg is in serum. Further, serum Mg is frequently still in the normal range even when an individual has actual Mg deficiency because concentrations of serum Mg are tightly regulated[31;47;48]. This is very similar to serum Ca, which is also tightly regulated in a narrow range[49-53] If serum Mg is under 0.7 mmol/l, a clinical diagnosis of Mg deficiency is made[31]. Serum Mg may be a good biomarker in the clinic for patients with severe symptomatic Mg deficiency[1]. Only 10% of all patients with Mg deficiency are likely to be diagnosed if the current critical value of 0.7 mmol/l is used[31]. Based on the data from a published study, if the critical value is elevated to 0.80 or 0.85 mmol/l, 34% or 40% of non-deficient subjects, respectively, were misclassified as Mg deficient[54]. Outside of serum, the remainder of the approximately 25 grams (g) of Mg in humans is in soft tissue (19%), bone (53%), and muscle (27%)[47;48]. It is not practical to routinely measure Mg in bone or muscle through biopsy.

A prior study found patients with Mg deficiency frequently had abnormal Mg tolerance tests in spite of a normal serum level of $Mg^{55;56}$. Moreover, Lukaski et al.[57], among 10 postmenopausal women, conducted a feeding study using low dietary Mg levels based on ordinary Western foods, in amounts taken by some Americans. After administration of this low Mg diet for three months, serum Mg was slightly reduced by 6% (p=0.07), but still within the normal range. However, there was a significant reduction in skeletal muscle Mg (p<0.05)[57]. Muscle Mg levels returned to normal after 49 days of a Mg repletion diet 57. Simsek et al. conducted a study among patients newly diagnosed with insulin dependent diabetes. They found that the plasma concentration of Mg was lower among diabetes patients than among normal controls, but, again, the level was still in the normal range. However, compared with normal controls, patients with diabetes had significantly higher Mg retention after intravenous (IV) infusion of Mg in the Mg tolerance test. A recent study found that the correlation between dietary intake of Mg and blood Mg was poor (r=0.02)[58]. In the ongoing trial, r=0.11 (p=0.66) was found between serum Mg and the Mg tolerance test. Thus, serum Mg is a poor test for discriminating Mg deficiency[1;32].

Although the Mg tolerance test is the most accurate approach currently available for measuring Mg status[1], it has several major limitations that prevent its adoption in both clinical and research practice. First, it cannot be used in patients with renal dysfunction or critical illness[30]. Secondly, it requires two 24-hour urine samples and a 4-hour IV Mg infusion,[1] making it impractical to implement in the clinic. Even in research trials using Mg supplementation, the Mg tolerance test cannot be used to measure Mg status at baseline or to monitor treatment effects or compliance because it substantially changes Mg status due to the 4-hour IV infusion of $Mg^{59}$.

Accordingly, there is a need in the art for a sensitive, specific, and more implementable method to assess Mg status and to treat Mg deficiency and prevent conditions associated therewith.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for detecting methylation biomarkers in a biological sample from a subject in need of assessment for magnesium deficiency status, methods of diagnosing magnesium deficiency, methods of diagnosing magnesium insufficiency, methods of treating magnesium deficiency, methods of diagnosing magnesium insufficiency, and methods of preventing or reducing a risk of developing a condition linked to magnesium deficiency.

In some embodiments, the presently-disclosed subject matter includes a method of detecting methylation biomarkers in a biological sample from a subject. In some embodiments, the method involves obtaining the biological sample from the subject, wherein the subject is in need of assessment for magnesium deficiency status; and detecting 5-hydroxymethylcytosine (5-hmC) and 5-methylcytosine (5-mC) methylation biomarkers and/or differentiating between 5-hydroxymethylcytosine (5-hmC) and 5-methylcytosine (5-mC) methylation biomarkers.

In some embodiments, the presently-disclosed subject matter includes an improved method for determining magnesium deficiency status in a subject as compared to detecting serum magnesium levels. In some embodiments the method involves detecting 5-hydroxymethylcytosine (5-hmC) and 5-methylcytosine (5-mC) methylation biomarkers and/or differentiating between 5-hydroxymethylcytosine (5-hmC) and 5-methylcytosine (5-mC) methylation biomarkers in a biological sample from the subject.

In some of the embodiments of the methods disclosed herein, bisulfite (BS) treatment of DNA is used to detect overall methylation biomarkers in the biological sample. In some of the embodiments of the methods disclosed herein, a TAB-Seq and TAB-Array protocol is used to differentiate between 5-hydroxymethylcytosine (5-hmC) and 5-methylcytosine (5-mC) methylation biomarkers in the biological sample.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
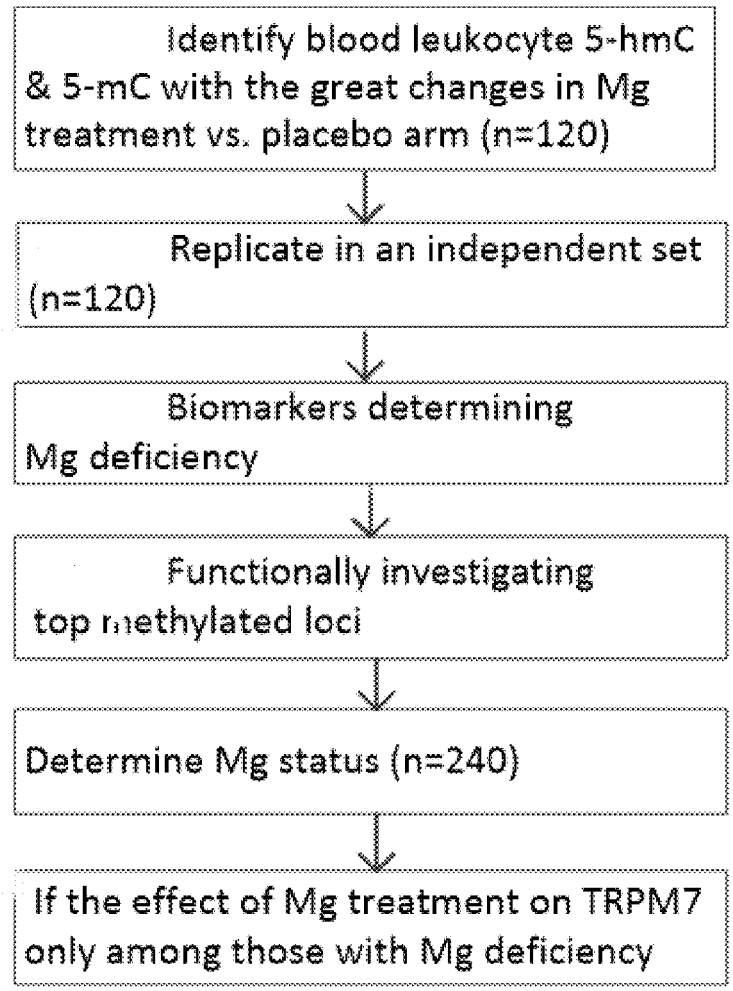
FIG. 1 is a flow chart showing the design of an exemplary study used to identify and assess methylation modifications disclosed herein for use in assessing magnesium status.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods for detecting methylation biomarkers in a biological sample from a subject in need of assessment for magnesium deficiency status, methods of diagnosing magnesium deficiency, methods of diagnosing magnesium insufficiency, methods of treating magnesium deficiency, methods of diagnosing magnesium insufficiency, and methods of preventing or reducing a risk of developing a condition linked to magnesium deficiency.

The presently-disclosed subject matter includes methods for detecting methylation biomarkers in a biological sample from a subject in need of assessment for magnesium deficiency status, methods of diagnosing magnesium deficiency, methods of diagnosing magnesium insufficiency, methods of treating magnesium deficiency, methods of diagnosing magnesium insufficiency, and methods of preventing or reducing a risk of developing a condition linked to magnesium deficiency.

In some embodiments, the presently-disclosed subject matter includes a method of detecting methylation biomarkers in a biological sample from a subject. In some embodiments, the method involves obtaining the biological sample from the subject, wherein the subject is in need of assessment for magnesium deficiency status; and detecting 5-hydroxymethylcytosine (5-hmC) and 5-methylcytosine (5-mC) methylation biomarkers and/or differentiating between 5-hydroxymethylcytosine (5-hmC) and 5-methylcytosine (5-mC) methylation biomarkers.

In some embodiments, the presently-disclosed subject matter includes an improved method for determining magnesium deficiency status in a subject as compared to detecting serum magnesium levels. In some embodiments the method involves detecting 5-hydroxymethylcytosine (5-hmC) and 5-methylcytosine (5-mC) methylation biomarkers and/or differentiating between 5-hydroxymethylcytosine (5-hmC) and 5-methylcytosine (5-mC) methylation biomarkers in a biological sample from the subject.

In some of the embodiments of the methods disclosed herein, bisulfite (BS) treatment of DNA is used to detect overall methylation biomarkers in the biological sample. In some of the embodiments of the methods disclosed herein, a TAB-Seq and TAB-Array protocol is used to differentiate between 5-hydroxymethylcytosine (5-hmC) and 5-methylcytosine (5-mC) methylation biomarkers in the biological sample.

In some of the embodiments of the methods disclosed herein, the methylation biomarkers include one or more of the methylation biomarkers set forth in Appendixes B-G.

In some of the embodiments, the methods disclosed herein further involve identifying the subject has having an MTT score of greater than or equal to 50 (magnesium deficiency), an MTT score of less than 50 and greater than or equal to 25 (magnesium insufficiency), or an MTT score of less than 25 (magnesium sufficiency). In some embodiments, the MTT score is determined using a method as described in Example 1.

In some of the embodiments, the methods disclosed herein further involve identifying the subject as having a magnesium deficiency when one or more of the methylation biomarkers set forth in any one of Tables 3-42 are detected in the sample. In some embodiments, two, three, four, five, six, seven, eight, nine, ten or more biomarkers are detected.

In some of the embodiments, the methods disclosed herein further involve administering an effective amount of magnesium to the subject identified as having a magnesium deficiency.

Some embodiments of the presently-disclosed subject matter include a method of preventing or reducing a risk of developing a condition linked to magnesium deficiency. In some embodiments, the methods involve determining magnesium deficiency status in a subject using the methods as disclosed herein; identifying the subject as having a magnesium deficiency when one or more of the methylation biomarkers associated with magnesium deficiency are detected in the sample; or identifying the subject as having a magnesium insufficiency when one or more of the methylation biomarkers associated with magnesium insufficiency are detected in the sample; and administering an effective amount of magnesium to the identified subject.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Magnesium Tolerance Test

In a magnesium tolerance test, a health care professional, such as a doctor, gives a participant a shot of a known amount of magnesium and then later uses the participant's urine to determine how much magnesium the participant's body retained, and how much the body eliminated.

If the participant's body retains most of the magnesium then it is assumed he or she needed it because of a deficiency, and if most of it is eliminated in the urine then it is assumed that the magnesium was not needed because he or she does not have a deficiency.

In an exemplary study as described herein, participants who completed the study received a schedule of planned magnesium tolerance tests on two consecutive days. A 24-hour urine sample was collected for determining the basal urinary magnesium excretion prior to the intravenous infusion of magnesium sulfate. Another 24-hour urine sample was obtained starting with the IV infusion.

Procedure

1. Collect 24-hour urine the day before the load test for basal magnesium and creatinine ratio.
2. Infuse 0.2 mEq (2.4 mg) elemental magnesium per kilogram of body weight in 50 ml of 5% detrose over 4 hours, which was conducted by nurses.
3. Collect urine (starting with infusion) for magnesium and creatinine for 24 hours
4. Check the blood pressure and heart rate for the participant before initiating magnesium sulfate IV. Infusion, and monitor the same vital signs in the course of infusion and within 1 hour following infusion completed.
5. Deliver two 24-hour urine samples to the Molecular Epidemiology Lab at Vanderbilt Epidemiology Center.

6. Handle and process the urine samples followed by the protocols, and then stored at −80° C. until urine magnesium/creatinine assay were applied.
7. Measure 24-hour urine magnesium, creatinine concentration using an atomic absorption spectrophotometer, provided by the Vanderbilt Pathology Laboratory Services.

Body Magnesium Status

1. Percentage magnesium retained is calculated by the formula below (Mg: magnesium)

$$\left[1 - \frac{(\text{post infusion } Mg \text{ excretion} - \text{basal } Mg \text{ excretion}*)}{\text{total } Mg \text{ infused}}\right] \times$$

$$100 * \text{basal } Mg \text{ excretion} =$$

$$\frac{\text{pre-infusion urine } Mg}{\text{pre-infused urine Creatinine}} \times \frac{\text{post-infusion 24 hour urine}}{\text{Creatinine}}$$

2. Criteria for magnesium status
   ≥50% retention at 24-hour urine: definite deficiency
   >25% to <50% retention at 24-hour urine: probable deficiency (insufficiency)
   ≤25% retention at 24-hour urine: normal (sufficiency)

Example 2

Blood Leukocyte Methylation as a marker of Mg Deficiency The majority of Mg is stored in bone[47;48]. Although it is very similar for Ca, the Ca content in bone is 40 to 50 times higher than Mg[60]. Thus, bone density is conventionally used to measure body status of Ca, but not Mg. About 30% of bone Mg is exchangeable and serves to stabilize serum concentration of Mg[61] because maintaining normal serum Mg is so critical that low serum Mg could be fatal[62;63] Thus, the serum Mg concentration is unlikely to significantly drop until the exchangeable stores of Mg in bone are used up. Diet with moderate depletion of Mg led to reduction in bone Mg content, but no significant change in serum Mg[64]. Recent studies found that Mg concentrations are essential for the differentiation[65], metabolism and activities[66] of human osteoclasts. Notably, hematopoietic stem cells (HSC) and osteoclasts are linked[67] and osteoclasts are important components of niches for HSCs in bone marrow, from which the majority of blood leukocytes (or white blood cells) develop.

It is known that DNA methylation changes are inducible by environmental exposures, including nutrients[34], and reversible when the exposure disappears[35]. Thus, methylation biomarkers have potential to be biomarkers of nutrient status. It is likely reduced Mg status in bone affects the differentiation (i.e. methylation) of HSC into blood leukocytes. Since the concentrations of Mg in bone drop long before serum Mg decreases, it is possible that methylation biomarkers in blood leukocytes affected by low Mg concentrations are promising biomarkers for Mg deficiency. Further, the rapid turn-over for the majority of blood leukocytes ranging from a few hours to a few days mean methylation biomarkers in leukocytes may readily reflect the changes in Mg status in bone. Thus, the present inventors contemplated sensitive methylomic markers in blood leukocytes for Mg deficiency.

5-hmC is a Newly Emerged Epigenetic Biomarker. DNA methylation at the cytosine in CpG dinucleotides, the most common epigenetic modification[68;69], regulates gene function without changing primary DNA coding sequence[70].

Although DNA methylation research has increased substantially over the past three decades, previous studies were limited by the inability to distinguish between the two major cytosine modifications: 5-methylcytosine (5-mC) and 5-hydroxymethylcytosine (5-hmC). 5-hmC can be generated by the oxidation of 5-mC through the ten-eleven translocation (Tet) family of enzymes (See FIG. 2)[70], and 5-hmC has distinct regulating functions in gene expression from 5-mC. In fact, it was not until very recently, in 2009 over 50 years after its discovery, that 5-hmC was "re-discovered" to be the 6th base in the human genome[71-73]. Although Tet proteins can further oxidize 5-hmC to 5-formylcytosine (5-fC) and 5-carboxylcytosine (5-caC), previous studies found the levels of 5-hmC were 100-fold higher than 5-fC and 5-caC[74-79]. Therefore, 5-mC and 5-hmC are the two major types of cytosine modifications in DNA.

Figure 4:
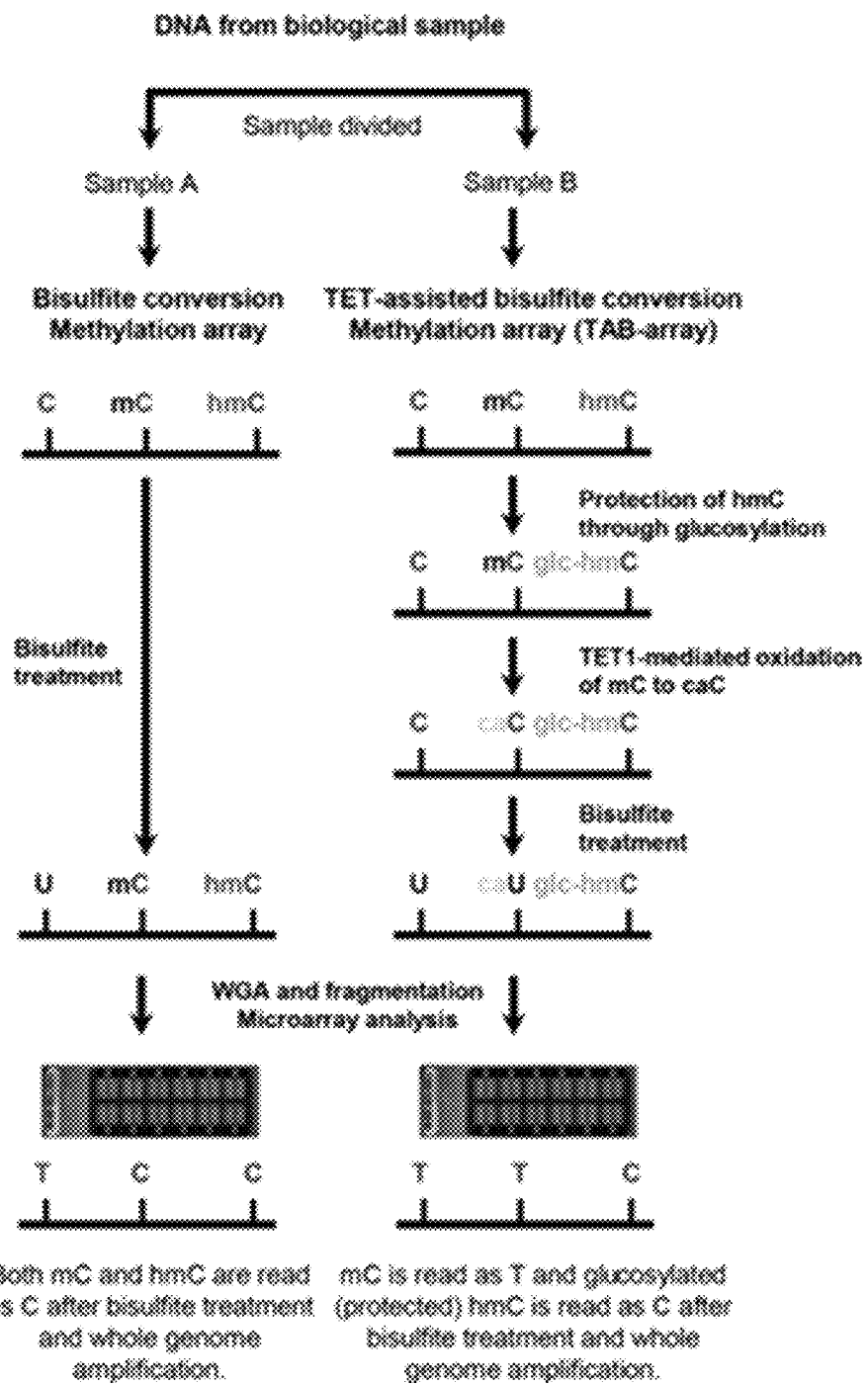
FIG. 4 depicts a TAB-array protocol to identify 5-hmC and 5-mC.
Figure 5A:
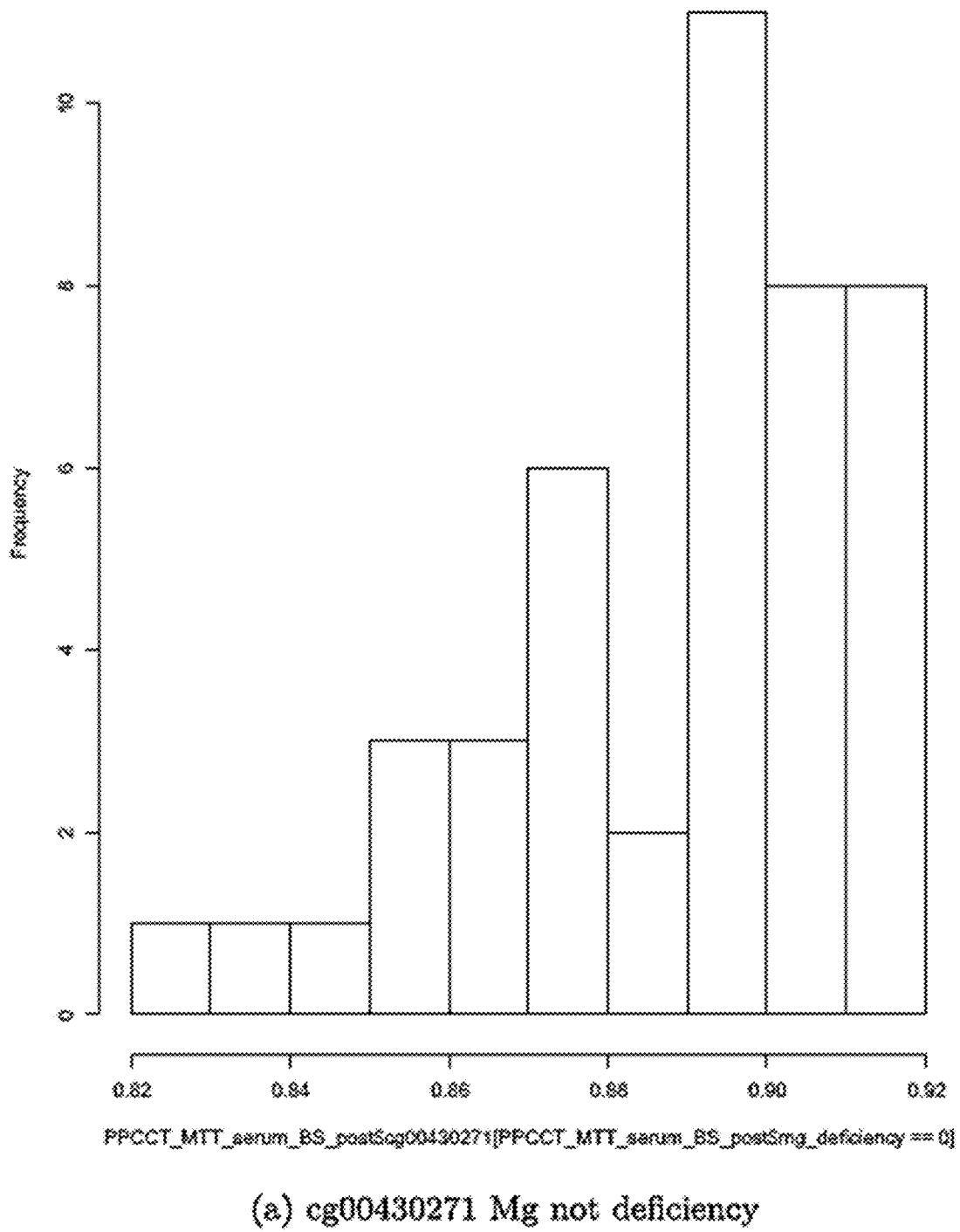
FIGS. 5A-5D include bar graphs depicting stratified distribution of exemplary markers cg00430271 and cg25731074.
Figure 5B:
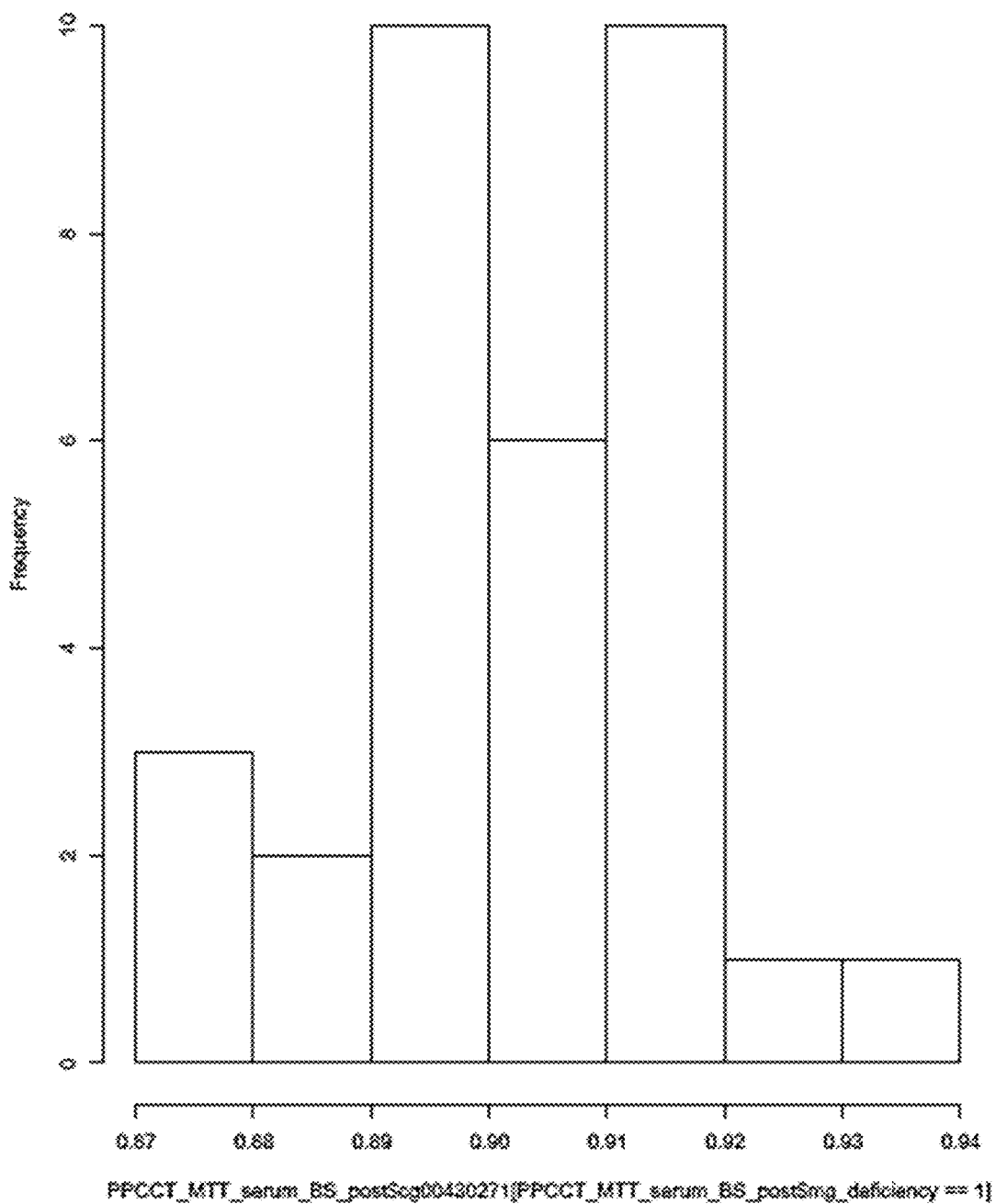
Figure 5C:
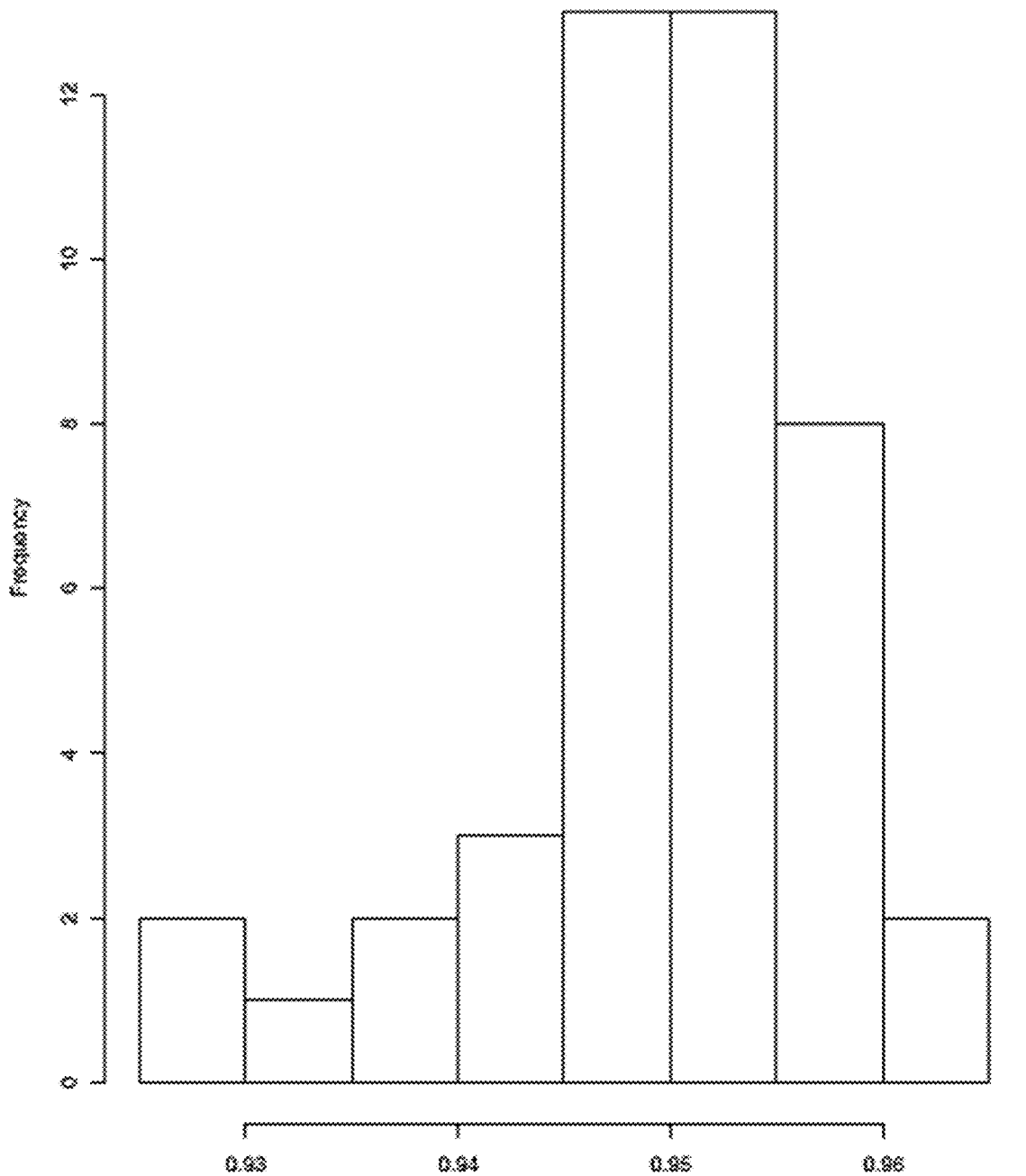
Figure 5D:
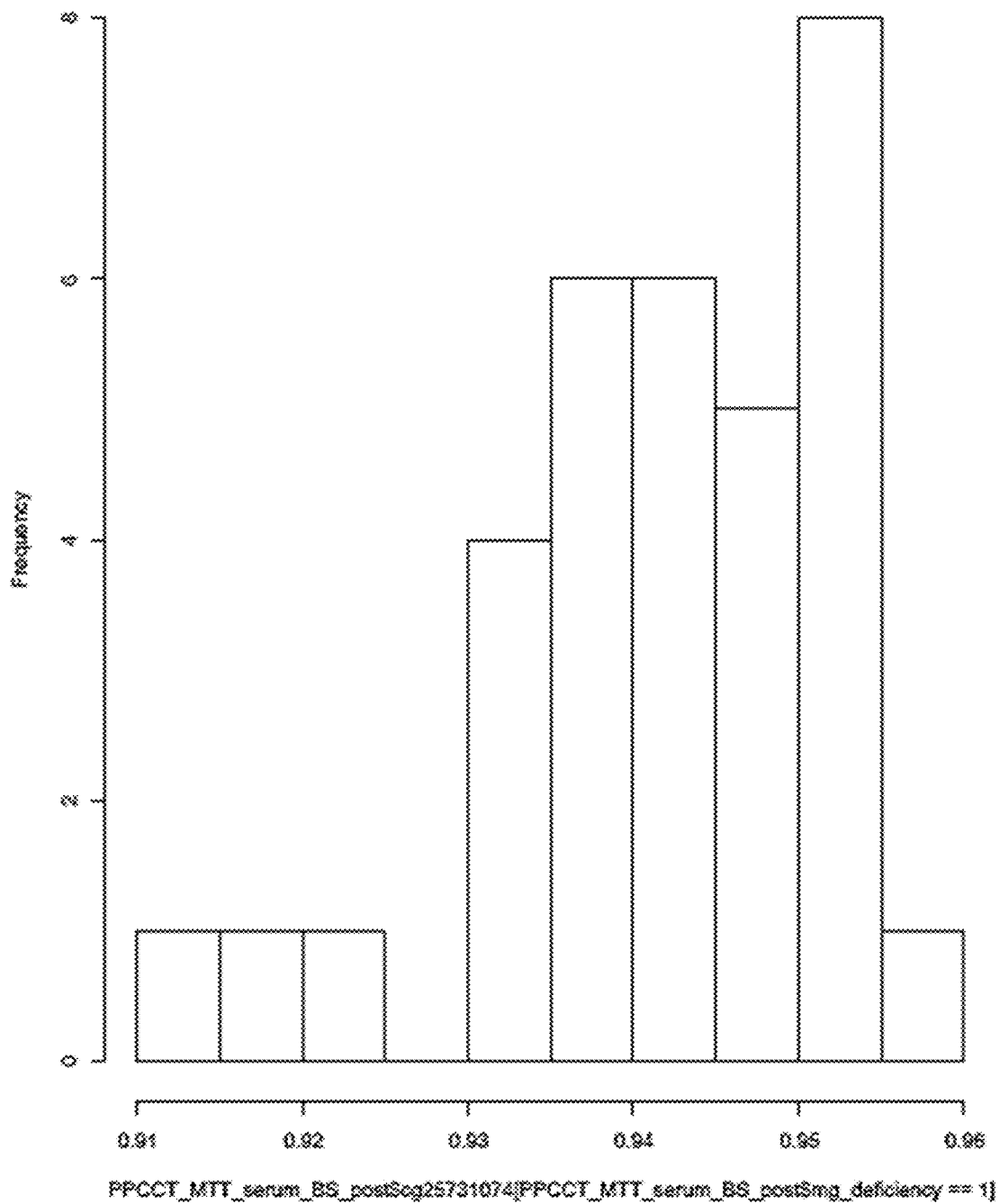

5-mC is often associated with suppressed gene expression[80;81] while 5-hmC is specifically enriched in expressed genes and plays a critical role in activating and/or maintaining gene expression[36;82]. Thus, without differentiating these two major cytosine modifications with distinct and opposite effects on gene expression, the findings from previous studies are difficult to interpret. In a recent study, the present inventors found 5-hmC may be a more sensitive marker than 5-mC for reflecting the changes in environment exposure. In fact, current epigenome-wide association study (EWAS) profiling platforms, including the widely-used Illumina Infinium HumanMethylation450 BeadChip[83] (HM450K), cannot distinguish between 5-mC and 5-hmC. However, as described herein, there is a unique technique, Tet-assisted Bisulfite Sequencing (TAB-Seq) and TAB-Array protocol[42-44] (See FIG. 4), which now allows accurate distinguishing of 5-hmC from 5-mC in the whole human genome.

Figure 2:
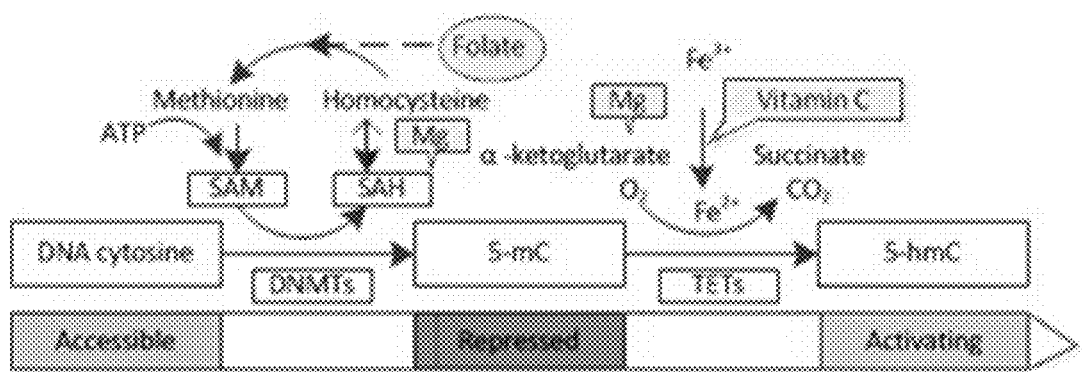
FIG. 2 illustrates the Mg and Cytosine Modification Pathway.

Mg, 5-hmC and 5-mC and Methylation Capacity. The present inventors found Mg intake is significantly and positively linked to global methylation pattern (i.e. LINE-1) and methylation biomarkers in genes/pathways with Mg as a co-factor. As shown in FIG. 2, two useful co-factors for the Tets to catalyze the oxidation of 5-mC to 5-hmC are Fe (iron)$^{2+}$ and α-ketoglutarate[70]. Previous studies found Mg affects metabolism of α-ketoglutarate[84;85]. Thus, it is very likely Mg may also affect the activity of Tets and, in turn, the oxidation of 5-mc to 5-hmC (See FIG. 2). It was found among those at risk of Mg deficiency Mg treatment may lead to substantially more changes, primarily upregulation, in 5-hmC (e.g. 296 genes with ≥4-fold changes in 5-hmC peaks in treatment arm compared to 39 genes in placebo arm) in colorectal tissues compared to the placebo arm (See section D1.1.3 in detail). Although the mostly up-modified changes in 5-hmC caused by Mg treatment are consistent with mostly up-modified changes also found in both in vitro and in vivo studies of vitamin C[86;87], the top differential CpG sites (either 5-mC or 5-hmC) linked to Mg treatment/intake do not overlap with those caused by vitamin C[86;87], indicating the changes in 5-mC or 5-hmC levels are unique to each nutrient. Thus, 5-mC and 5-hmC may be used as both specific and sensitive biomarkers for Mg status.

S-adenosylmethionine (SAM), the second most widely used substrate molecule in the cell[88], is the methyl donor for almost all methylation reactions including DNA methylation (FIG. 2), which has profound physiologic consequences. S-adenosylhomocysteine (SAH) is a product of the transfer of a methyl group from SAM to 80 other molecules and is the metabolic precursor of all homocysteine (Hcy) produced in the body in an irreversible reaction in which the equilibrium favors SAH. SAM has two products, a methylated molecule, such as DNA, and SAH. As SAH level increases, it prevents conversion of SAM to SAH[89;90]. This, in turn, results in decrease in DNA methylation[91;92]. Based on a strong biological basis, it is not surprising that positive associations between DNA methylation and circulating levels of SAM and SAH have been observed in previous studies. Thus, SAM and SAH levels are considered as the methylation capacity[93-97]. In a pilot study conducted in a randomized clinical trial, it was found that Mg treatment affected SAH level vs. placebo arm in those at risk of Mg deficiency.

Methylation Markers Can be Altered by the Changes in Nutritional Status in a Dose-Response Manner. There is mounting evidence that nutritional factors differentially involved directly or indirectly in methylation and hydroxymethylation affect 5-mC or 5-hmC. In the following, folate and vitamin C will be used as examples to present further evidence that 5-hmC and 5-mC can serve as sensitive biomarkers of Mg status.

Folate indirectly affects SAH (FIG. 2) and has been widely studied for its potential effect in methylation. The findings from human, animal and in vitro studies indicate folate affects global as well as gene-specific and (gene) region-specific methylation biomarkers. An in vitro study using the sensitive Comet approach found folate depletion led to "a dose-dependent response" in hypomethylation while folate supplementation reversed the global and (gene) region specific (e.g. p53) hypomethylation caused by folate depletion[98]. Similar to in vitro findings, there are two human randomized trials of moderate folate depletion followed by moderate folate repletion[99;100]. Both trials consistently found that leukocyte genomic methylation[99;100] decreased in response to moderate folate depletion. One trial[99] found folate repletion reversed the hypomethylation caused by folate depletion while the other trial[100] indicated it may take longer to reverse hypomethylation among elderly women. The authors concluded that "DNA methylation status may be used as a functional indicator of moderately depleted folate status"[100]. Consistent with this finding, other randomized trials found folate supplementation did not change leukocyte methylation in normal subjects[101;102], but reversed methylation among high risk populations (e.g. those with hyperhomocysteinemia)[103;104] However, none of these previous studies were able to differentiate 5-hmC from 5-mC.

Vitamin C is important in reducing $F^{3+}$ to $F^{2+}$, one of two key co-factors for the Tets to catalyze the oxidation of 5-mC to 5-hmC while Mg affects the other key cofactor (i.e. α-ketoglutarate)[70] (FIG. 2). One study published in Nature[86], found vitamin C supplementation enhanced Tet activity and, in turn, altered DNA methylation and gene expression pattern in embryonic stem cells. Similar to the observed Mg effect on 5-hmC, vitamin C supplementation led to a genome-wide increase in 5-hmC but a decrease in 5-mC. The change in 5-hmC in response to vitamin C supplementation was quicker than that on 5-mC. Both 5-hmC and 5-mC changes are correlated with over 2-fold changes, primarily up-modifications, in expressions of approximately 200 genes. Furthermore, the effect of vitamin C supplementation was reversible on both 5-hmC and 5-mC in promoter, and 5-hmC also more rapidly responded to vitamin C withdrawal than 5-mC. Further, the observed changes in 5-hmC are specific to vitamin C, but not other antioxidants (i.e. glutathione, selenite, vitamin E, vitamin B1, L-carnitine and α-lipoic acid). Another study[87] found similar results in embryonic stem cells. In the mouse model deficient in vitamin C synthesis, although there were overlaps between 5-mC changes and 5-mC alterations caused by vitamin C treatment, specific genes with elevated 5-hmC in response to vitamin C treatment were identified. Further, vitamin C supplementation significantly elevated 5-hmC concentrations in all three tissues, but decreased 5-mC in two tissues; indicating 5-hmC may be a more sensitive biomarker than 5-mC to reflect changes in nutritional status.

From the examples of folate and vitamin C it can be seen that 1) changes are specific to individual nutrients and these methylation changes locate in specific genes and gene regions, 2) changes are dependent on dose and duration, 3) changes likely have functional significance (i.e. linked to gene expression), 4) changes could differ by tissue or cell type, and 5) 5-hmC may more rapidly and sensitively respond than 5-mC to changes in nutritional status. These indicate 5-hmC and 5-mC biomarkers respond to nutritional status in a dose-response and nutrient-specific manner.

Unlike folate, which may only indirectly affect SAH, or vitamin C, which solely influences the conversion from 5-mC to 5-hmC, Mg may affect leukocyte differentiation in bone and circulation SAH as well as the conversion from 5-mC to 5-hmC. As such, the combination of 5-hmC and 5-mC biomarkers in blood leukocytes are contemplated to serve as sensitive biomarkers unique for Mg deficiency. Further, these 5-hmC and 5-mC biomarkers have functional significance given its regulatory function of gene expression.

During Mg depletion process, Mg concentration in bone drops long before a significant decrease in serum $Mg^{64}$. Reduced Mg concentrations in bone are contemplated to affect the differentiation of bone HSC, the primary source of blood leukocytes and, thus, lead to modifications in blood leukocyte 5-mC and 5-hmC. Further, due to the rapid turn-over in blood leukocytes, the status of 5-mC and 5-hmC in blood leukocytes may readily reflect bone Mg status. This is supported by the four lines of novel pilot finding suggesting that Mg treatment affects both methylation capacity and the conversion from 5-mC to 5-hmC among those at high risk of Mg deficiency (D1.1). Thus, it is further contemplated that blood 5-mC and 5-hmC biomarkers, particularly when combined with serum Mg, are more sensitive and specific than serum Mg to differentiate Mg deficiency vs. non-deficiency. Thus, the proposed study uniquely identifies methylation biomarkers for Mg deficiency. Unlike serum Mg, the 5-mC and 5-hmC biomarkers have potential functional significance given their regulatory function of gene expression. The investigation includes studying the role of top modified CpG (5-hmC and 5-mC) loci in gene expression to identify functional biomarkers for Mg deficiency.

The current EWAS profiling platforms, including the widely-used Illumina HM450K[83], cannot distinguish 5-hmC from 5-mC, two major types of modified cytosines with distinct regulating functions[36;36;73;80-82;105]. A state of the art technique[42-44] has been developed, which now allows accurate distinguishing of 5-hmC from 5-mC methylation in the whole human genome. In addition, integrative analyses will be conducted to determine whether an index developed from combinations of biomarkers from multiple pathways achieve better prediction than a single biomarker. Finally, a personalized prevention application will be investigated by examining whether the newly identified biomarkers can be used to identify individuals who derive chemopreventive benefit for CRC from Mg supplementation.

Importance of Methylomic Biomarkers in Clinics and Screening. In 2014, a screening multi-target tool which combines aberrantly methylated BMP3 and NDRG4 promoter regions with mutations in KRAS and β-actin has been approved by the FDA for colorectal neoplasia screening in asymptomatic individuals at average risk of CRC. Using this tool, a study published in *New England Journal of Medicine*[106] found DNA tests (i.e. DNA methylation and mutations) have much higher sensitivity (Se) and specificity (Sp) to identify CRC or precancerous lesions than clinically used hemoglobin biomarkers in fecal samples with a Se of 92.3% for CRC. A qPCR-based approach was used to determine DNA 5-mC biomarkers and DNA mutations. The success of this screening tool indicates it is practical to use an index derived from combined methylation biomarkers in clinical or general populations. Similar to this study, a qPCR-based approach is used to quantify both 5-mC and 5-hmC biomarkers. A composite index combining 5-mC and 5-hmC biomarkers with serum Mg levels will be used to identify individuals with Mg deficiency. The clinical use of this composite index is tested for the prevention of CRC among those with Mg deficiency.

Importance of a Sensitive Biomarker of Mg Status for Disease Prevention and DRI Revision. Previous studies indicate that the associations between Mg intake and risk of CRC and cardiometabolic disease completely differ by deficient or sufficient Mg status[29]. Even among US and Western populations at high risk of Mg deficiency, individual studies have generated inconsistent results on the association between Mg intake with colorectal neoplasia[4-6], T2D[19], coronary heart disease[19;24-27] and stroke[28]. Similarly, the associations have also been inconsistent by using serum/plasma[27;58;107-113]. One possible explanation for the inconsistent findings is that Mg intake may not be a sensitive measure of Mg status. A recent study found that the correlation between dietary Mg and blood Mg was poor (r=0.02)[58]. On the other hand, only about 0.3% of the total body Mg is in serum and concentrations of serum Mg are tightly regulated[31;47;48].

In addition to Mg intake, many other factors affect body overall Mg status. These factors include 1) other minerals (e.g. Ca)[49;51;114-119]; 2) alcohol drinking[120;121]; 3) disease conditions (e.g. type 2 diabetes)[122]; 4) medications, such as medications commonly used to treat reflux symptoms (i.e. proton pump inhibitors)[123-126], thiazide diuretics (i.e. one antihypertensive medication)[127], cisplatin-based chemotherapy medications[128], cetuximab[129] (i.e. a monoclonal antibody inhibitor of the epithelial growth factor receptor), lipid lowering medications (e.g. statins)[130]; and 5) genetic polymorphisms[131] (e.g. TRPM7[49;132]). Thus, an accurate measure of overall body Mg status which can reflect many known and unknown factors affecting Mg status is necessary.

Although the Mg tolerance test is currently the most accurate approach to measure Mg status[1], this approach has several major limitations which prevent its adoption in the clinic, prospective human studies, and randomized clinical trials (See B1.3 for details). Therefore, it is critical to develop simpler, more sensitive, and more specific biomarkers for Mg deficiency which reflect the aggregate factors affecting Mg status.

In growing recognition of the importance of Mg in human health, very recently, Mg was selected for updating of the recommended intake level by the US and Canadian Federal Dietary Reference Intake (DRI) Committee. However, previous studies have used either Mg intake or serum Mg and generated inconsistent results using these metrics on which the new DRI review will also be based. Thus, the new DRI will still be controversial because, due to non-differential misclassification, it is likely that the true associations of low Mg status with CRC or cardiometabolic disease risk may be much stronger than those observed. As such, in April 2015, a workshop has been organized by the American Society for Nutrition (ASN) to discuss the challenges in accurately measuring Mg status. If the proposed study succeeds, a new composite index will be developed. The composite index will be used in randomized or cohort studies to accurately examine the associations and understand the etiology between Mg status and the above-mentioned common diseases, which will lay a solid foundation for future DRI revision.

Importance of Sensitive and Functional Biomarkers for Precision Medicine. Using the Mg tolerance test[1], studies conducted in 5 different US populations have found mean retention rates of Mg in excess of 50%, which is the criterion to define Mg deficiency[2]. In an ongoing trial, it was found, after 12-week Mg supplementation, that 42% of individuals still had Mg deficiency. These findings indicate a large proportion, but not all of the US population, is at risk of Mg deficiency. As mentioned, in contrast to the US population at high risk of Mg deficiency, in populations with lower intake of Ca and medications related to Mg status, high Mg intake has been related to an increased risk of total mortality (e.g. total cancer, CRC, and CVD), particularly when Ca intake is low[29].

Thus, a simpler biomarker or index will be useful for the success of personalized medicine for the prevention of Mg deficiency and other common diseases (i.e. CRC and CVD) related to Mg deficiency. In this application, a sensitive composite index is proposed to identify individuals who still have serum Mg within a normal range, but have a reduced body Mg status which already leads to 5-mC and 5-hmC modifications in DNA. Further, the functional significance of these biomarkers will be examined by profiling gene expression. Thus, the functional significance of the biomarkers included in the final composite index will be known. This new index can be used to identify individuals with Mg deficiency in the general population, clinics, or clinical trials for personalized prevention that maximizes efficacy and minimizes adverse effects. The effect of Mg supplementation on biomarkers related to CRC carcinogenesis is examined.

Mg treatment on plasma methylation capacity. Mg is essential in over 300 biological activities[149], including multiple processes in genomic stability[38;39]. A study was conducted to evaluate whether Mg supplementation affects SAM and SAH (biomarkers for methylation capacity) among those at high risk of Mg deficiency. The finding suggests change in Mg status causes alteration in methylation capacity and, in turn, leads to methylation changes.

Figure 3:
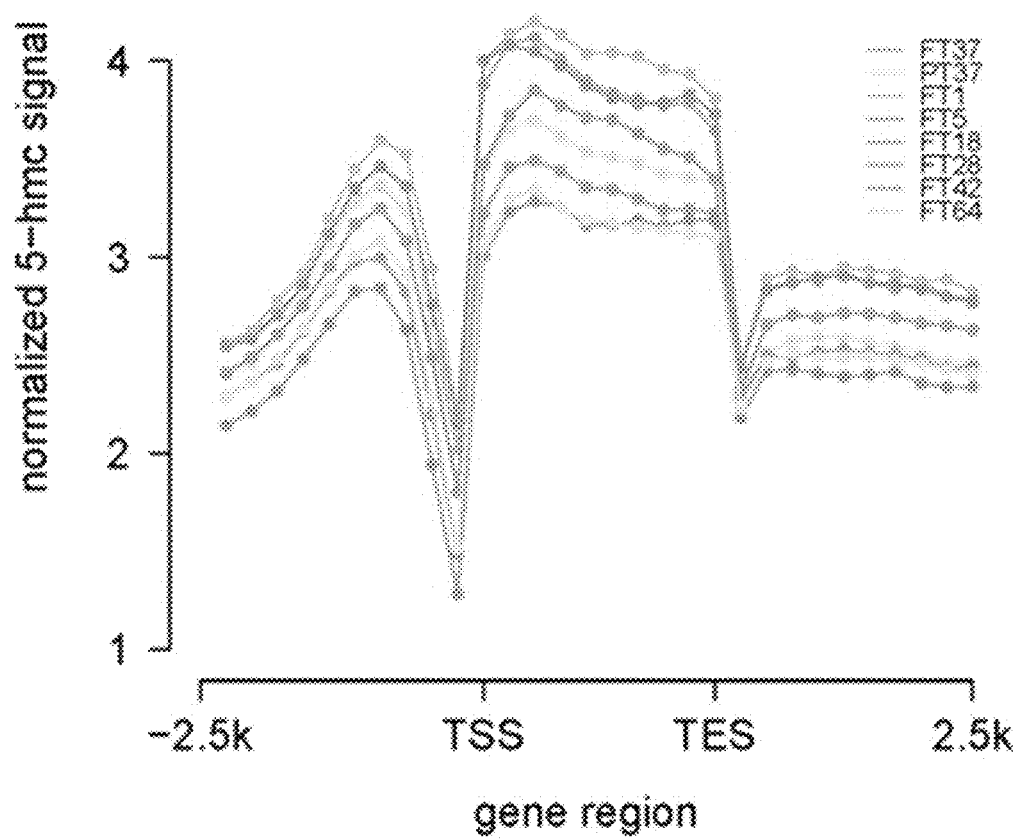
FIG. 3 includes the results of a 5-hmC affinity enrichment sequencing analysis of rectal tissues.

5-hmC alterations induced by Mg treatment. As mentioned, due to technological limitations, distinguishing 5-hmC from 5-mC has only recently been possible. Using the technology an evaluation was conducted of 5-hmC in normal rectal mucosa collected at baseline from 7 participants of the PPCCT. 5-hmC-specific affinity pull-down[142] samples were sequenced using the Illumina next-generation sequencing (50 bp single-end). The raw sequencing reads were mapped to the human genome reference (hg19) using Bowtie2[153]. 5-hmC peaks (i.e. enriched 5-hmC regions) were then called using the MACS algorithm[154]. There are two important findings. 1) There are approximately 13,000-15,000 high quality 5-hmC peaks across the genomes at p<1e-5 calculated by MACS. 2) The distribution plot in FIG. 3 shows that there is apparent inter-individual variation in 5-hmC levels with a distinct genic distribution (e.g. much higher in the gene body).

Genome-wide 5-hmC was also measured in pre- (i.e. baseline) and post-treatment rectal tissues (i.e. after 3-month Mg supplementation). In this analysis, one individual was included in the treatment arm and the other in the placebo arm. Two-hundred ninety-six (296) and 1271 genes were found with ≥4-fold or ≥3-fold changes in 5-hmC levels from baseline, respectively, in the treatment arm compared to 39 and 176 in the placebo arm (Table 1). Thus, the treatment arm has a much larger number of affected genes than the placebo arm.

Furthermore, the majority of the changes found in 5-hmC caused by Mg treatment are up-modifications, very consistent with findings from in vitro and in vivo studies of vitamin C treatment[86;87]. Functional annotation analysis using the NIH/DAVID tool[155] indicated that the 296 genes at ≥4-fold in the treatment arm were enriched with such Gene Ontology biological processes as "regulation of Ras protein signal transduction", "regulation of small GTPase mediated signal transduction", "regulation of ARF protein signal transduction", and "Wnt receptor signaling pathway" relative to the genome reference at a FDR <10%, indicating that, although with a limited sample size, differential 5-hmC modifications in relevant pathways (e.g. Ras and GTPase as Mg plays a key role in energy metabolism[37-41]) could be detected with Mg treatment.

TABLE 1

Genes with greatest changes in 5-hmC peaks

| Fold change in 5-hmC | Number of genes in the treatment arm | Number of genes in the placebo arm |
|---|---|---|
| ≥4 | 296 | 39 |
| ≥3 | 1271 | 176 |

5-hmC may be a sensitive biomarker of environmental exposure. In a recent study, global 5-mC and 5-hmC were measured in blood DNA by ELISA and evaluated the effects of ambient particulate matter (PM10) on blood global 5-mC and 5-hmC levels in two highly exposed groups of adults in Beijing, China from The Beijing Truck Driver Air Pollution Study[156-158]. The study found that exposure to ambient PM10 increased 5-hmC over time from 20% to 133% with p values ranging from 0.01 to <0.001), but not of 5-mC. This finding suggests 5-hmC is a sensitive biomarker in reflecting the changes in environmental exposure.

The finding suggests 5-hmC is a sensitive biomarker in reflecting environmental change. Low Mg intake was linked to blood leukocyte global methylation and differentially methylated CpGs in genes with Mg as a co-factor. Although Mg intake is not an accurate measure of Mg status, it was found in a trial that 3-month Mg treatment significantly altered SAH, one biomarker of methylation capacity (D1.1.1) and may lead to changes in 5-hmC (D1.1.3) among individuals at risk of Mg deficiency. The change in SAH was about 20% while 296 genes had ≥4-fold change in 5-hmC levels. On the other hand, in a previous human study, 3-month Mg depletion reduced serum Mg from 0.85 to 0.81 mmol/L (p=0.07), and subsequent 49 days of Mg repletion increased the serum Mg by 6% from 0.81 to 0.86 (p=0.06)[57]. Taken together, the findings, although preliminary, indicate that the combination of 5-hmC and 5-mC may serve as a more sensitive biomarker of Mg deficiency than serum Mg.

When comparing the top differential CpGs (5-hmC or 5-mC) linked to Mg treatment/intake and those affected by vitamin C[86;87], there was not any overlap found, indicating the 5-mC or 5-hmC can be specific biomarkers for Mg status. Further, the 5-mC and 5-hmC biomarkers have potential functional significance.

High total Ca or Mg was reported to be related to a reduced risk of colorectal adenoma or hyperplastic polyps when the Ca/Mg ratio was below the median[159]. In a subsequent analysis in a large-scale randomized clinical trial in the US, it was found that Ca treatment significantly reduced colorectal adenoma recurrence risk only when the baseline dietary Ca/Mg ratio was under 2.6[160]. Furthermore, it was found that the Ca/Mg intake ratio significantly interacted with the common Thr1482Ile polymorphism (rs8042919, G→A) in TRPM7 (transient receptor potential melastatin 7), in relation to both adenomas and hyperplastic polyps. Based on these findings, a trial is being conducted among 240 colorectal polyp patients with Ca/Mg ratio ≥2.6. Results will determine 1) if reducing the Ca/Mg ratio through Mg supplementation affects biomarkers related to Mg homeostasis and CRC carcinogenesis (e.g. TRPM7, apoptosis, cell proliferation and COX expression in rectal biopsies); and 2) whether the effects differ by TRPM7 genotype.

The study is a double-blind, placebo-controlled randomized trial conducted in Nashville, TN, comparing 12 weeks of Mg supplementation with placebo. Participants are generally healthy, have a history of colorectal polyps, are aged 40 to 85 years, do not have histories of cancer, IBD and colon resection, haveTRPM7 genotypic data, are not using anti-coagulant medications, and have a baseline Ca/Mg ratio ≥2.6, among other inclusion and exclusion criteria. 240 participants are expected to be recruited and randomized to either Mg treatment or placebo with permuted-block randomization.

A Mg tolerance test, the most accurate approach to evaluate Mg nutriture, is conducted at the end of trial. Participants are collecting a 24-hour urine sample at home. The next day, at their clinic visit, after confirmation of adequate renal function, participants receive 0.2 mmol/kg body weight of Mg sulfate in 500 ml of 5% glucose by intravenous infusion over a four hour period. A second 24-hour urine sample begins at the time of the infusion and continues through the next day. For the Mg tolerance test, the participant's percent retention is calculated by the following formula:

[1−(post infusion Mg excretion-pre infusion Mg excretion)/total Mg infused]×100.

A retention of ≥50% indicates Mg deficiency[161]. 42% of the subjects are Mg deficient at the end of the trial (blinded analysis). The Pearson's correlation between serum Mg and the Mg tolerance test was found to be only 0.11 (p=0.66) among the 18 participants with both serum Mg and the Mg tolerance test. Based on current participation, it is estimated about 100 participants will complete the Mg tolerance test (before the proposed study starts).

Magnesium supplementation. In the parent study, participants are using either daily Mg glycinate capsules or identical-appearing lactose placebo. Mg doses average 205 mg. Ca, Mg, and vitamin D intakes are determined through the administration of six days of dietary record-based 24-hour recalls (two prior to intervention and four during intervention) which include supplements. Pill counts and compliance calls are conducted throughout the study to monitor compliance.

Data collection. An interviewer-administered questionnaire includes family history of cancer and lifestyle information, including smoking and alcohol histories. During the in-person visits to the clinic, information is also collected regarding recent, long-term, and current medication use, anthropometric measurements, and diet in addition to the six days of dietary recalls described above.

Biological sample collection/storage. Fasting blood sample (separated into serum, plasma and buffy coat with leukocytes) and 8 rectal biopsies are collected at day 0, and again at the conclusion of the intervention (week 12), and are stored on ice until processed. All blood samples are processed within 4-6 hours. All samples are placed in long-term storage in −80° C. freezers.

Overview of the Study Design. An initial study was completed with more than 200 participants. The study design is summarized in FIG. 1. An unbiased EWAS study is conducted to identify 5-hmC/5-mC biomarkers of Mg deficiency by taking a four-phase approach.

By using the TAB-Seq and TAB-Array protocol (See FIG. 4)[42-44], both 5-hmC and 5-mC biomarkers are measured in half of the participants in the parent study. 5-mC and 5-hmC biomarkers with the greatest changes in blood leukocyte DNA are identified, comparing Mg treatment vs. placebo arm.

These findings are replicated in the remaining half of participants using the TAB-Seq and TAB-Array protocol (See FIG. 4)[42-44].

Confirmed 5-hmC/5-mC biomarkers are tested alone or combined with serum Mg to differentiate Mg status with higher sensitivity and specificity than serum Mg, among 100 participants with the Mg tolerance test. Further, integrative analysis will be conducted to identify the combinational biomarker index from different pathways that may have even higher sensitivity and specificity. The final composite index will be generated from 5-mC and 5-hmC biomarkers from multiple pathways and serum Mg[106].

The top 20 modified CpG loci are selected from those identified and then their functional significance is examined by evaluating their correlation with their gene expression levels to functionally evaluate the findings.

Biomarker Assays

Bioassay quality control. Samples are organized in treatment-placebo (i.e. one treatment arm with one placebo arm) sets (4 samples in each set: 2 from pre-, and 2 from post-treatment) to minimize between-assay variation. Extracted DNA samples and plasma samples are shipped on dry ice via overnight to the labs in two locations. To control for batch-to-batch variability, samples from each set are analyzed in the same run. Quality control (QC) samples (5% of samples) will be added to each batch of samples to be assayed. Lab staff will be blinded to the sample status (in treatment or placebo arms, or QC).

Measurement of DNA Methylation and Hydroxymethylation.

Genomic DNA is extracted from buffy coat fractions collected in the PPCCT using a QIAamp DNA mini-kit (Qiagen Inc, Valencia, CA) according to the manufacturer's protocol[159].

Unbiased interrogation screen of DNA methylation and hydroxymethylation will be undertaken across a wide swath of the genome. The TAB-Array assay combines the Illumina HM450K array profiling and the TAB-Seq assay[42]. The TAB-Array protocol has been successfully used to profile 5-hmCs in human cells[44] and has been incorporated into Illumina's protocol (See FIG. 3). Briefly, each sample will be profiled twice using the HM450K array according to the Illumina recommended protocol at the Northwestern University Genomics Core. To distinguish 5-hmC from 5-mC, besides one regular bisulfite conversion-based profiling for 5-mC, the second HM450K profiling will be performed after the TAB assay, which employs the feature that genomic 5-hmC loci are protected by glucosylation from Tet conversion[43]. Specifically, in the TAB assay, genomic DNA is treated with β-glucosyltransferase (β-GT) to conjugate all 5-hmC residues to glucose. The DNA is then treated with Tet1 to convert 5-mC and 5-formylcytosine (5-fC) to 5-carboxylcytosine (5-caC), while cytosine and glycosylated 5-hmC remain unaffected. During subsequent bisulfite treatment, unmodified cytosines and 5-caC are converted to uracil or 5-carboxyuracil (5-caU), respectively, whereas 5-hmC remains protected by glycosylation. The location of 5-hmC is then indicated by a cytosine in the HM450K array profiling results since all other cytosine species (C, 5-mC, 5-fC, and 5-caC) have been converted to thymine. Data generated from these two array profiling assays in each sample will then allow for distinguishing these two modified cytosines.

Bisulfite sequencing (for 5-mC) and the TAB-Seq (for 5-hmC) is conducted to confirm the TAB-Array results. The top 20 differential CpG loci are selected to be evaluated using both approaches in at least 30 random samples. Correlation with the TAB-Array data will be used to confirm the reliability of profiling.

Measurement of Plasma Methionine Cycle Metabolites.

LC/MS-MS. All protocols for SAM and SAH analysis are well-established and are used on a regular basis. Stable-isotope dilution liquid chromatography-electrospray tandem mass spectrometry (LC-ESI-MS/MS) will be used to determine methionine, SAM and SAH in plasmas[95;162]. A second LC-ESI-MS/MS method will be used to determine plasma total homocysteine (tHcy)[163]. Table 2 indicates the multiple reaction monitoring transitions (m/z) for each metabolite and respective stable isotope internal standard and retention time.

QC samples will be included at the start and end of each batch of plasma samples to be analyzed. All QC data must be within two standard deviations of the preset limits (inter-assay variation) indicated in Table 2. Ten (10) paired samples collected before and the day following fasting were also compared, and a bowel cleansing preparation and found the correlation between the two collection times was high (r=0.89 for SAH, r=0.79 for SAM) consistent with a previous study with repeated measurements of SAM and SAH[164].

TABLE 2

LC-MS/MS MRM methods and assay performance for methionine cycle metabolites

| Analyte | MRM (m/z) | Labeled Isotope | Labeled Isotope (m/z) | RT (min) | Inter-assay Precision | |
|---|---|---|---|---|---|---|
| | | | | | Level 1 (CV %) | Level 2 (CV %) |
| Methionine | 150 → 104 | $^2H_3$-Methionine | $^2H_3$-Methionine | 5.0 | 7.0% | 5.9% |

TABLE 2-continued

LC-MS/MS MRM methods and assay performance for methionine cycle metabolites

| Analyte | MRM (m/z) | Labeled Isotope | Labeled Isotope (m/z) | RT (min) | Inter-assay Precision Level 1 (CV %) | Inter-assay Precision Level 2 (CV %) |
|---|---|---|---|---|---|---|
| SAM | 399 → 250 | $^2H_3$-SAM | $^2H_3$-SAM | 5.7 | 7.6% | 5.5% |
| SAH | 385 → 136 | $^2H_4$-SAH | $^2H_4$-SAH | 5.4 | 8.1% | 6.8% |
| Hcy | 136 → 90 | $^2H_4$-Hcy | $^2H_4$-Hcy | 0.9 | 7.9% | 6.9% |

Serum Mg is measured by standard method on the Beckman DXC 800 chemistry analyzer provided by the Vanderbilt Pathology Laboratory Services with an intra-assay coefficient of variation of $2.0^{165}$.

Functional validation by gene expression. To examine the functional significance of the top differentially modified loci identified, real-time (RT)-PCR is performed to measure the expression levels of 20 selected genes in leukocytes in all 200+ participants.

Expression of genes located locally (e.g. 10 kb) will be evaluated to the differentially modified CpGs. Briefly, RNA will be obtained from leukocytes collected in the PPCCT using the RNeasy Plus Mini Kits (Qiagen Inc, Valencia CA). mRNA will be reverse transcribed to cDNA using the Agilent Biosystems High Capacity Reverse Transcription Kit. qRT-PCR will be performed for each gene together with an endogenous control using TaqMan Gene Expression Assays following standard TaqMan protocols. Each sample will be run on a minimum of two plates in triplicates with standard deviation controlled to less than 15%.

Example 3

In PPCCT study, 250 participants were enrolled, randomly allocated to treatment or placebo and had the 1st dose of intervention. Two hundred forty (240) completed week 12 data collection (the end of the study intervention and the primary data collection time point). Ten (10) participants withdrew from the study due to: moving (1), change of mind (4), side effects (5). Among the 240, 17 participants had compliance less than 90% based on pill counts.

MTT was conducted on 78 subjects in PPCCT. After completion of the 12-week intervention, MTT was conducted among those who were willing to participate and 77 participants finished the test. In the test, two 24 hour urine samples were obtained, one prior to the intravenous infusion of magnesium sulfate and the other starting with the IV infusion. Urine magnesium level was measured using 7D70 Magnesium Reagent Kit from Abbot Laboratories (Abbott Park, TL). The method utilizes an arsenzo dye which binds preferentially with magnesium. The absorbance of the arsenazo-magnesium complex is measured at 572 nm and is proportional to the concentration of magnesium present in the sample.

Their diagnosis was made by serum magnesium concentration. Serum magnesium concentration was determined using 7D70 Magnesium Reagent Kit from Abbot Laboratories (Abbott Park, TL) the assay was conducted at the Vanderbilt Pathology Laboratory Services. The method utilizes an arsenzo dye which binds preferentially with magnesium. The absorbance of the arsenazo-magnesium complex is measured at 572 nm and is proportional to the concentration of magnesium present in the sample. This diagnosis criterion is considered the gold standard. Unfortunately, this gold standard diagnosis sometimes cannot be obtained early to guide treatment decision.

The diagnostic values of the identified methylation markers was determined to distinguish Mg-deficiency (>=50%) and Mg-insufficiency (>=25%) early Statistical Methods To discover the top picks in the bisulfite (BS) dataset, various approaches are contemplated.

In one approach, a 3-phase study is carried out. The participants (N=240) are first divided in the randomized trial into two groups (n=120 in each group) by medium enrollment date.

In Phase 1, methylation biomarkers with the greatest changes in blood leukocyte DNA comparing Mg treatment vs. placebo (n=114) were identified. For differential methylation analysis, the t-test was used for change score (change score=post âĂŞ pre) using limma software. The selected sites include 100,766 CpG sites out of 836,588 with a Type I error of 0.1.

In Phase 2, the Phase 1 findings (i.e. 100,766 CpG sites) were replicated in an independent set of participants (n=110) from the PPCCT and 5,539 CpG sites were found out of 100,766 at a Type I error rate of 0.05. The analyses were limited to the CpG sites for which the changes caused by Mg treatment were in the same direction for both phases 1 and 2 and for which the difference between the treatment arm and the placebo arm were also in the same direction for both phases 1 and 2. Finally, 4,449 CpG sites that changed with Mg treatment vs. placebo were identified.

For those selected biomarkers, logistic models were fit to describe the probability of the Mg status being deficient (or insufficient) ($Y_i$=1 for MTT less than 50% for subject i, alternatively, $Y_i$=1 for MTT less than 25% for subject i), otherwise $Y_i$=0 (nondeficient/noninsufficient).

There are two steps in the analyses. Step one is data reduction. LASSO and elasticnet regressions are conducted for variable selection. In step two, the selected variables are used to develop a classification rule for Mg status or a prediction model for MTT.

The LASSO and elasticnet regressions are penalized logistic regressions or GLM conducted as:

$$\hat{\beta} = \underset{\beta}{\mathrm{argmin}}\{-[\log \text{ likelihood } (\beta)]/n + \lambda[(1-\alpha)/2\|\beta\|_2^2 + \alpha\|\beta\|_1]\} \quad (1)$$

where $$\|\beta\|_2 = \left(\sum_{j=1}^{p} \beta_j^2\right)^{1/2},$$

$$\|\beta\|_1 = \sum_{j=1}^{p} |\beta_j|,$$

and log likelihood (β) is the logistic likelihood function.

In (1), α=1 gives the Least Absolute Shrinkage and Selection Operator (LASSO) regression (Tibshirani, 1996) and α<1 gives us elasticnet (Zou and Hastie, 2005) regression. Parameter λ is chosen through k-fold cross-validation.

The accuracy of the classification rule is measured by calculating the rule's discrimination using area under receiver operating characteristic (ROC) curve or concordance (c-index). The rule's calibration demonstrated will be calculated with a smooth nonparametric calibration curve or scatter plot of estimated versus observed outcome. The calibration and discrimination of the rule will be internally validated using bootstrap resampling in order to estimate the likely performance of the rule on a new sample of patients from the same patient stream (Sections 10.8 and 10.9 of Harrell 2001xxx). Future prospective investigations will be planned to externally validate the classification rule.

In Phase 3, the 4,449 CpG sites were used to predict Mg deficiency status at the end of the PPCCT trial. Mg deficiency status was measured by the Mg tolerance test results among 77 participants who completed the two 24-hour urine samples and a 4-hour IV Mg infusion71. Using logistic regression models by adjusting for serum Mg measured at the end of the trial and least absolute shrinkage and selection operator (LASSO) to reduce potential overfitting, 84 CpG sites are reported over minimum mean cross-validated error by LASSO.

Finally, via LASSO composite indices of multiple methylation biomarkers in predicting Mg deficiency status were identified.

As noted above, in the first approach, the original dataset was imputed, then biomarker sites were selected by phase1/phase2 and directional restriction from 836588 sites.

The logistic model for Mg deficiency/insufficiency status was fist via penalized maximum likelihood (1). The regularization path was computed for LASSO with α=1 and for the elasticnet with α=0.25, 0.5, 0.75.

There were 4449 sites selected from 836588 sites by phase1/phase2 and directional restriction. For Mg deficiency, LASSO/elasticnet regression fits pick 84 sites.

Table 3 presents the methylation markers selected by LASSO or elasticnet at A value that minimizes the cross-validation misclassification rate.

follows. Table 4 presents AUC for some combination of the methylation markers selected by LASSO or elasticnet at λ value that minimizes the cross-validation misclassification rate.

TABLE 4

Logistic fit of some combination of selected sites for Mg deficiency in BS

| site 1 | site 2 | site 3 | site 4 | AUC |
|---|---|---|---|---|
|  |  |  |  | 0.8230028 |
| cg01842741 | cg10051786 |  |  | 0.8195592 |
| cg03084350 | cg11333566 |  |  | 0.8140496 |
| cg11840205 | cg128000781 |  |  | 0.8092287 |
| cg00430271 | cg26335127 |  |  | 0.8057851 |
| cg06922496 | cg26864174 |  |  | 0.8019972 |
| cg00430271 | cg10951786 |  |  | 0.8016529 |
| cg12187394 | cg25731074 |  |  | 0.8016529 |
| cg00924527 | cg11840205 |  |  | 0.7982094 |
| cg01842741 | cg25731074 |  |  | 0.7975207 |
| cg06022406 | cg11333566 | cg18056714 |  | 0.8801653 |
| cg00430271 | cg11840205 | cg26335127 |  | 0.8794766 |
| cg00430271 | cg11840205 | cg25731074 |  | 0.8753444 |
| cg00430271 | cg15916745 | cg25731074 |  | 0.8746556 |
| cg00430271 | cg01842741 | cg25731074 |  | 0.8698347 |
| cg04578283 | cg11840205 | cg14265145 |  | 0.8670799 |
| cg00430271 | cg04578283 | cg11840205 |  | 0.8050138 |
| cg00430271 | cg18917736 | cg25731074 |  | 0.8643251 |
| cg00430271 | cg03084350 | cg25731074 |  | 0.8626033 |
| cg00430271 | cg04987122 | cg25731074 |  | 0.8626033 |
| cg00430271 | cg04386563 | cg11840205 | cg25731074 | 0.9256198 |
| cg00430271 | cg02074074 | cg11840205 | cg26335127 | 0.9214876 |
| cg00430271 | cg04386563 | cg11840205 | cg26335127 | 0.9187328 |
| cg00430271 | cg15916745 | cg18956714 | cg25731074 | 0.9173554 |
| cg00430271 | cg01110440 | cg11840205 | cg26335127 | 0.9139118 |
| cg00430271 | cg01110440 | cg01842741 | cg10951786 | 0.9097796 |
| cg00430271 | cg11840205 | cg15916745 | cg25731074 | 0.9084022 |
| cg00430271 | cg11840205 | cg26335127 | cg26864174 | 0.9077135 |
| cg00430271 | cg01842741 | cg23260330 | cg25731074 | 0.9070248 |
| cg00430271 | cg10127610 | cg12187394 | cg25731074 | 0.9056474 |

Detailed logistic regression results of some interesting combination of markers in Table 5 were double checked.

TABLE 3

Variables selected by LASSO/elasticnet for Mg deficiency in BS site Name

| | | | | | | |
|---|---|---|---|---|---|---|
| cg05019905 | cg25731074 | cg06407417 | cg11840205 | cg06295308 | cg06922496 | cg10350957 |
| cg00924527 | cg12496307 | cg26335127 | cg00576263 | cg07739604 | cg11333566 | cg00430271 |
| cg07777270 | cg10951786 | cg12087941 | cg18219712 | cg18534872 | cg23260330 | cg21636911 |
| cg26074539 | cg01407874 | cg22236894 | cg02635020 | cg18947305 | cg10983873 | cg02276825 |
| cg00023056 | cg18427968 | cg16477259 | cg12187394 | cg19608680 | cg24351671 | cg04987122 |
| cg17813946 | cg01110440 | cg26864174 | cg15021089 | cg18917736 | cg15916745 | cg03084350 |
| cg21457401 | cg01152729 | cg12800781 | cg14265145 | cg10127610 | cg04578283 | cg12062489 |
| cg01842741 | cg11295178 | cg20613400 | cg18082638 | cg01501912 | cg24423359 | cg14950072 |
| cg18664866 | cg10613701 | cg16418754 | cg18956714 | cg15210809 | cg26186954 | cg02469161 |
| cg23725734 | cg12660093 | cg26794993 | cg17379666 | cg17500902 | cg08108029 | cg21397480 |
| cg13663211 | cg06756499 | cg10231801 | cg26909602 | cg04729491 | cg17370417 | cg13992360 |
| cg04386563 | cg02074074 | cg06894687 | cg03901836 | cg26951706 | cg17313709 | cg23194229 |

Pick 2, 3, or 4 from the union of 84 sites, run logistic regression model and some combination examples are as The stratified distribution of marker cg00430271 and cg25731074 A listed in FIG. 5.

TABLE 5 some logistic regression models for Mg deficiency in BS

| | Logistic Model | AUC |
|---|---|---|
| Mg deficiency - | cg00430271 | 0.6646 |
| | cg25731074 | 0.7094 |
| | cg00430271 + cg25731074 | 0.8230 |
| | cg00430271 + cg11840205 + cg25731074 | 0.8753 |
| | cg00430271 + cg04386563 + cg11840205 + cg25731074 | 0.9256 |

For Mg insufficiency, LASSO/elasticnet regression fits pick 117 sites. Table 6 presents the methylation markers selected by LASSO or elasticnet at λ value that minimizes the cross-validation missclassification rate.

TABLE 6

Variables selected by LASSO/elasticnet for Mg insufficiency in BS site Name

| | | | | |
|---|---|---|---|---|
| cg17102582 | cg12600069 | cg24216889 | cg06407417 | cg10270306 |
| cg13914600 | cg22997415 | cg05031696 | cg09858749 | cg18956714 |
| cg25033719 | cg00823602 | cg19422947 | cg16722435 | cg05382973 |
| cg17965622 | cg02795691 | cg16244786 | cg16731240 | cg10231801 |
| cg02117656 | cg03955314 | cg13233725 | cg25557858 | cg23812215 |
| cg11567608 | cg01336268 | cg01100448 | cg14584422 | cg15645605 |
| cg04416635 | cg01382875 | cg26331945 | cg10855773 | cg20658450 |
| cg05019905 | cg09486166 | cg23060646 | cg12513738 | cg07908870 |
| cg02506875 | cg06108900 | cg15652683 | cg11078674 | cg18233497 |
| cg24624572 | cg19594772 | cg16619071 | cg16418754 | cg12477050 |
| cg27198485 | cg07425005 | cg15182613 | cg22315933 | cg26335127 |
| cg01850352 | cg05630957 | cg11921952 | cg16393730 | cg13823415 |
| cg02469161 | cg17441998 | cg26794993 | cg14901226 | cg08539620 |
| cg16464483 | cg23358699 | cg27632704 | cg02117713 | cg02276825 |
| cg01135781 | cg18790771 | cg23260330 | cg11513221 | cg12502223 |
| cg21178653 | cg10581837 | cg20931474 | cg10848640 | cg17399385 |
| cg16477259 | cg07273980 | cg01076051 | cg04589248 | ch.16.50217098R |
| cg12259593 | ch.2.54406426R | cg02192472 | cg00843631 | cg10242496 |
| cg01657422 | cg16589555 | cg19446777 | cg13431373 | cg12284971 |
| cg22333471 | cg06719651 | cg02461690 | cg25392154 | cg24985235 |
| cg09223811 | cg21107235 | cg00946712 | cg15721020 | cg16790645 |
| cg05264252 | cg04165824 | cg00145955 | cg00884973 | cg18670278 |
| cg03307560 | cg10159922 | cg21882593 | cg16577509 | cg04321753 |
| cg04645444 | cg01588826 | | | |

Pick 2, 3, or 4 from the union of 117 sites, run logistic regression model and some combination examples are as follows. Table 7 presents AUC for some combination of the methylation markers selected by LASSO or elasticnet at λ value that minimizes the cross-validation missclassification rate.

TABLE 7

Logistic fit of some combination of selected sites for Mg insufficiency in BS

| site 1 | site 2 | site 3 | site 4 | AUC |
|---|---|---|---|---|
| cg10231801 | cg16722435 | | | 0.9048964 |
| cg10231801 | cg25033719 | | | 0.8935970 |
| cg04165824 | cg10231801 | | | 0.8907721 |
| cg12259593 | cg16790645 | | | 0.8841808 |
| cg10231801 | cg12259593 | | | 0.8822976 |
| cg10231801 | cg16619071 | | | 0.8794727 |
| cg06843631 | cg10231801 | | | 0.8771186 |
| cg05264252 | cg10231801 | | | 0.8766478 |
| cg04321753 | cg10231801 | | | 0.8747646 |
| cg10231801 | cg16577509 | | | 0.8747646 |
| cg10231801 | cg16722435 | cg25033719 | | 0.9576271 |
| cg10231801 | cg23358699 | cg25033719 | | 0.9529190 |
| cg12259593 | cg16790645 | cg19422947 | | 0.9500942 |
| cg10231801 | cg13914600 | cg25033719 | | 0.9463277 |
| cg00823602 | cg02795691 | cg10231801 | | 0.9458569 |
| cg10231801 | cg10270306 | cg16722435 | | 0.9444444 |
| cg04165824 | cg10231801 | cg25557858 | | 0.9435028 |
| cg10231801 | cg12259593 | cg16790645 | | 0.9435028 |
| cg02795691 | cg10231801 | cg16722435 | | 0.9425612 |
| cg07908870 | cg10231801 | cg16619071 | | 0.9387947 |
| cg00823602 | cg02795691 | cg10231801 | cg25033719 | 0.9783427 |
| cg00823602 | cg02795691 | cg10231801 | cg16722435 | 0.9764595 |
| cg02795691 | cg10231801 | cg13914600 | cg25033719 | 0.9726930 |
| cg02795691 | cg10231801 | cg16722435 | cg24216889 | 0.9717514 |
| cg02795691 | cg10231801 | cg16722435 | cg18956714 | 0.9708098 |
| cg00823602 | cg02795691 | cg10231801 | cg15645605 | 0.9680266 |
| cg02795691 | cg10231801 | cg16722435 | cg25033719 | 0.9689266 |
| cg00823602 | cg10231801 | cg16731240 | cg25033719 | 0.9679849 |
| cg02795691 | cg10231801 | cg17965622 | cg25033719 | 0.9679849 |
| cg02795691 | cg10231801 | cg10270306 | cg16722435 | 0.9670433 |

In approach 2, all 836,588 CpG sites are used to predict Mg deficiency status at the end of the PPCCT trial. Using logistic regression models and LASSO, 118 sites are reported over minimum mean cross-validated error by LASSO.

The original dataset of 836588 sites was inputted without further selection. The logistic model for Mg deficiency/insufficiency status was fit via penalized maximum likelihood (1). The regularization path was computed for LASSO with α=1 and for the elasticnet with α=0.25, 0.5, 0.75 in (1).

For Mg deficiency, LASSO/elasticnet regression fits pick 118 sites.

Table 8 presents the methylation markers selected by LASSO or elasticnet at λ value that minimizes the cross-validation missclassification rate.

TABLE 8

| Variables selected by LASSO/elasticnet for Mg deficiency in BS site Name | | | | |
|---|---|---|---|---|
| cg17102582 | cg12600069 | cg24216889 | cg06407417 | cg10270306 |
| cg13914600 | cg22997415 | cg05031696 | cg09858749 | cg18956714 |
| cg25033719 | cg00823602 | cg19422947 | cg16722435 | cg05382973 |
| cg17965622 | cg02795691 | cg16244786 | cg16731240 | cg10231801 |
| cg02117656 | cg03955314 | cg13233725 | cg25557858 | cg23812215 |
| cg11567608 | cg01336268 | cg01100448 | cg14584422 | cg15645605 |
| cg04416635 | cg01382875 | cg26331945 | cg10855773 | cg20658450 |
| cg05019905 | cg09486166 | cg23060646 | cg12513738 | cg07908870 |
| cg02506875 | cg06108900 | cg15652683 | cg11078674 | cg18233497 |
| cg24624572 | cg19594772 | cg16619071 | cg16418754 | cg12477050 |
| cg27198485 | cg07425005 | cg15182613 | cg22315933 | cg26335127 |
| cg01850352 | cg05630957 | cg11921952 | cg16393730 | cg13823415 |
| cg02469161 | cg17441998 | cg26794993 | cg14901226 | cg08539620 |
| cg16464483 | cg23358699 | cg27632704 | cg02117713 | cg02276825 |
| cg01135781 | cg18790771 | cg23260330 | cg11513221 | cg12502223 |
| cg21178653 | cg10581837 | cg20931474 | cg10848640 | cg17399385 |
| cg16477259 | cg07273980 | cg01076051 | cg04589248 | ch.16.50217098R |
| cg12259593 | ch.2.54406426R | cg02192472 | cg00843631 | cg10242496 |
| cg01657422 | cg16589555 | cg19446777 | cg13431373 | cg12284971 |
| cg22333471 | cg06719651 | cg02461690 | cg25392154 | cg24985235 |
| cg09223811 | cg21107235 | cg00946712 | cg15721020 | cg16790645 |
| cg05264252 | cg04165824 | cg00145955 | cg00884973 | cg18670278 |
| cg03307560 | cg10159922 | cg21882593 | cg16577509 | cg04321753 |
| cg04645444 | cg01588826 | | | |

Pick 2, 3, or 4 from the union of 118 sites, run logistic regression model and some combination examples are as follows.

Table 9 presents AUC for some combination of the methylation markers selected by LASSO or elasticnet at λ value that minimizes the cross-validation missclassification rate.

TABLE 9

| Logistic fit of some combination of selected Mg deficiency in BS | | | | |
|---|---|---|---|---|
| cg18910313 | cg26286077 | | | 0.9049587 |
| cg05095647 | cg11368923 | | | 0.9039256 |
| cg11368923 | cg14844977 | | | 0.9028926 |
| cg11368923 | cg17431860 | | | 0.9001377 |
| cg16106313 | cg18910313 | | | 0.8980716 |
| cg03597723 | cg11368923 | | | 0.8973829 |
| cg06045761 | cg21494343 | | | 0.8973829 |
| cg02692511 | cg22798756 | | | 0.8929063 |
| cg06213635 | cg14844977 | | | 0.8925620 |
| cg05863683 | cg25498045 | | | 0.8911846 |
| cg02692511 | cg08878802 | cg16106313 | | 0.9662534 |
| cg03597723 | cg05095647 | cg11368923 | | 0.9648760 |
| cg05095647 | cg11613875 | cg18746826 | | 0.9600551 |
| cg06213635 | cg14450620 | cg14844977 | | 0.9593664 |

TABLE 9-continued

| Logistic fit of some combination of selected Mg deficiency in BS | | | | |
|---|---|---|---|---|
| cg00327506 | cg06840298 | cg17162453 | | 0.9586777 |
| cg03043243 | cg06292683 | cg18746826 | | 0.9566116 |
| cg01331062 | cg03941824 | cg04285064 | | 0.9559229 |
| cg03597723 | cg11368923 | cg17338208 | | 0.9552342 |
| cg03597723 | cg11368923 | cg17431860 | | 0.9552342 |
| cg06213635 | cg20384683 | cg21369695 | | 0.9552342 |
| cg01331062 | cg03043243 | cg06292683 | cg23862011 | 0.9931129 |
| cg05095647 | cg11368923 | cg11613875 | cg18746826 | 0.9917355 |
| cg16106313 | cg16484042 | cg18746826 | cg25739288 | 0.9910468 |
| cg01331062 | cg03597723 | cg05095647 | cg11368923 | 0.9903581 |
| cg01331062 | cg03043243 | cg06292683 | cg25498045 | 0.9889807 |
| cg06045761 | cg11613875 | cg15613012 | cg16106313 | 0.9889807 |
| cg01331062 | cg05095647 | cg06045761 | cg11613875 | 0.9862259 |
| cg01331062 | cg03043243 | cg06292683 | cg12064372 | 0.9855372 |
| cg05095647 | cg11613875 | cg14131256 | cg18746826 | 0.9855372 |
| cg01331062 | cg03043243 | cg06292683 | cg18746826 | 0.9848485 |

For Mg insufficiency, LASSO/elasticnet regression fits pick 252 sites.

Table 10 presents the methylation markers selected by LASSO or elasticnet at λ value that minimizes the cross-validation missclassification rate.

TABLE 10

| Variables selected by LASSO/elasticnet for Mg insufficiency in BS site Name | | | | | | |
|---|---|---|---|---|---|---|
| cg10055621 | cg02563636 | cg21057880 | cg08520660 | cg12269394 | cg21710569 | cg15482690 |
| cg16643840 | cg07442759 | cg06809055 | cg10054262 | cg11018337 | cg18867708 | cg19051504 |
| cg02074478 | cg03906697 | cg16103996 | cg13133961 | cg06756169 | cg26744387 | cg22511432 |
| cg05542957 | cg24613479 | cg16762072 | cg12038684 | cg12307823 | cg25623271 | cg17545218 |
| cg18522266 | cg10575376 | cg19851029 | cg17102089 | cg19300474 | cg22740700 | cg23186116 |
| cg10191772 | cg05995260 | cg19354851 | cg01654446 | cg10308906 | cg27145495 | cg18469778 |
| cg15848792 | cg09232499 | cg02550027 | cg10044839 | cg21258377 | cg15367487 | cg11058730 |
| cg05798223 | cg26874164 | cg01520858 | cg13792460 | cg22736872 | cg13751775 | cg11166759 |
| cg18763656 | cg10732215 | cg10672567 | cg23792658 | cg04822405 | cg23823879 | cg09950256 |

TABLE 10-continued

Variables selected by LASSO/elasticnet for Mg insufficiency in BS site Name

| | | | | | | |
|---|---|---|---|---|---|---|
| cg21923861 | cg07525971 | cg02919116 | cg23806084 | cg24659093 | cg23686983 | cg10091335 |
| cg11953383 | cg17265279 | cg03826594 | cg27148952 | cg10261952 | cg15724296 | cg14416747 |
| cg23377495 | cg26608883 | cg16879197 | cg09142260 | cg21062661 | cg09603594 | cg07584331 |
| cg20832125 | cg12278099 | cg10072995 | cg17089444 | cg08960045 | cg26142604 | cg17164520 |
| cg21565543 | cg20568108 | cg04536393 | cg06217399 | cg15269754 | cg02941697 | cg01785473 |
| cg12573318 | cg12566078 | cg11713008 | cg18467358 | cg12259892 | cg12988231 | cg19560579 |
| cg03021910 | cg09030187 | cg04127455 | cg27005373 | cg23471617 | cg16458834 | cg08452613 |
| cg01516591 | cg13075456 | cg12925904 | cg27413396 | cg12614789 | cg04379126 | cg15711208 |
| cg02845345 | cg06203009 | cg12943441 | cg25498045 | cg14999518 | cg08198851 | cg05314679 |
| cg05888518 | cg00826536 | cg17094127 | cg07604566 | cg26722858 | cg03389215 | cg24343524 |
| cg24001601 | cg27266060 | cg02235760 | cg19667913 | cg26990667 | cg22776504 | cg02795691 |
| cg25670545 | cg05836790 | cg08159120 | cg23251282 | cg13861802 | cg00415057 | cg00088575 |
| cg07410597 | cg21997109 | cg23175573 | cg04344303 | cg19859445 | cg05682319 | cg19021236 |
| cg26903218 | cg20772106 | cg10498390 | cg19301992 | cg00170421 | cg25976440 | cg21150271 |
| cg24210818 | cg22173794 | cg17630144 | cg17692879 | cg16753420 | cg04175109 | cg27457631 |
| cg03428945 | cg06045761 | cg17547883 | cg04559604 | cg00017630 | cg25997661 | cg20926461 |
| cg07189587 | cg08143605 | cg00999950 | cg04763519 | cg17678928 | cg15002115 | cg00908117 |
| cg11620475 | cg02658969 | cg02341645 | cg20100675 | cg27661212 | cg07360304 | cg01705888 |
| cg02805354 | cg26291276 | cg12568536 | cg01480545 | cg02916173 | cg15727032 | cg12319618 |
| cg16896144 | cg23564460 | cg00401721 | cg14764085 | cg16372825 | cg05101463 | cg16258229 |
| cg24613906 | cg24073042 | cg20533553 | cg22617044 | cg19160694 | cg14526241 | cg22699815 |
| cg25654768 | cg16664915 | cg07973125 | cg18515510 | cg18964630 | cg15595495 | cg25843873 |
| cg00181497 | cg10406482 | cg21198880 | cg14451730 | cg02742551 | cg11498908 | cg12080079 |
| cg16181135 | cg18436123 | cg13988329 | cg06626140 | cg11440629 | cg20659752 | cg05083647 |
| cg21545071 | cg07015412 | cg00482488 | cg15133564 | cg22914616 | cg01797652 | cg13649960 |
| cg19701205 | cg03408135 | cg17239714 | cg15131187 | cg26655697* | cg06509153 | cg12875665 |
| cg11304573 | cg10544554 | cg29886858 | cg27115113 | cg27055732 | cg17585910 | cg17747199 |

Pick 2, 3, or 4 from the union of 252 sites, run logistic regression model and some combination examples are as follows.

Table 11 presents AUC for some combination of the methylation markers selected by LASSO or elasticnet at λ value that minimizes the cross-validation missclassification rate.

TABLE 11

Logistic fit of some combination of selected sites for Mg insufficiency in BS

| site 1 | site 2 | site 3 | site 4 | AUC |
|---|---|---|---|---|
| cg10055621 | cg11166759 | | | 0.9538606 |
| cg07360304 | cg12038684 | | | 0.9463277 |
| cg10055621 | cg19021236 | | | 0.9425612 |
| cg12269394 | cg15367487 | | | 0.9425612 |
| cg12269394 | cg14416747 | | | 0.9416195 |
| cg01785473 | cg20832125 | | | 0.9406780 |
| cg00482488 | cg08520660 | | | 0.9392655 |
| cg12269394 | cg18763656 | | | 0.9387947 |
| cg19560579 | cg24343524 | | | 0.9387947 |
| cg05995260 | cg25843873 | | | 0.9378531 |
| cg08520660 | cg16643840 | cg21710569 | | 0.9698082 |
| cg10055621 | cg16643840 | cg21710569 | | 0.9698082 |

TABLE 11-continued

Logistic fit of some combination of selected sites for Mg insufficiency in BS

| site 1 | site 2 | site 3 | site 4 | AUC |
|---|---|---|---|---|
| cg10055621 | cg12269394 | cg16643840 | | 0.9623352 |
| cg08520660 | cg12269394 | cg16643840 | | 0.9613936 |
| cg02563636 | cg08520660 | cg16643840 | | 0.9604520 |
| cg08520660 | cg10055621 | cg16643840 | | 0.9557439 |
| cg08520660 | cg16643840 | cg21057880 | | 0.9557439 |
| cg10055621 | cg16643840 | cg21057880 | | 0.9548023 |
| cg02563636 | cg08520660 | cg12269394 | | 0.9519774 |
| cg02563636 | cg10055621 | cg12269394 | | 0.9519774 |
| cg02563636 | cg10055621 | cg16643840 | cg21710569 | 0.9934087 |
| cg02563636 | cg08520660 | cg16643840 | cg21710569 | 0.9868173 |
| cg02563636 | cg08520660 | cg10055621 | cg16643840 | 0.9839925 |
| cg02563636 | cg10055621 | cg12269394 | cg16643840 | 0.9821092 |
| cg02563636 | cg08520660 | cg12269394 | cg16643840 | 0.9802260 |
| cg08520660 | cg12269394 | cg16643840 | cg21710569 | 0.9802260 |
| cg10055621 | cg12269394 | cb16643840 | cg21710569 | 0.9802260 |
| cg08520660 | cg10055621 | cg16643840 | cg21710569 | 0.9792844 |
| cg08520660 | cg12269394 | cg16643840 | cg21057880 | 0.9774011 |
| cg08520660 | cg16643840 | cg21057880 | cg21710569 | 0.9774011 |

For Mg deficiency, LASSO/elasticnet regression fits pick 72 sites using approach 1 (i.e., two-phase study).

TABLE 12

Variables selected by LASSO/elasticnet for Mg deficiency in BS

| | | | | | |
|---|---|---|---|---|---|
| "cg07121807" | "cg08001123" | "cg15863924" | "cg20435284" | "cg18315623" | "cg25428389" |
| "cg15152945" | "cg20858033" | "cg10350957" | "cg04780086" | "cg10983873" | "cg09182447" |
| "cg24687894" | "cg25368651" | "cg04671914" | "cg16052920" | "cg00430271" | "cg18477635" |
| "cg18947305" | "cg19103546" | "cg10432364" | "cg03889299" | "cg23691220" | "cg25040679" |
| "cg17105557" | "cg01037314" | "cg23997664" | "cg14282531" | "cg11441416" | "cg07731404" |
| "cg24202000" | "cg11049018" | "cg01716499" | "cg26196087" | "cg27123859" | "cg13207790" |
| "cg20805104" | "cg16737267" | "cg24687806" | "cg07582923" | "cg06108900" | "cg14227325" |
| "cg14883993" | "cg20653128" | "cg15347131" | "cg26864174" | "cg18956714" | "cg24833731" |
| "cg03240920" | "cg12660093" | "cg13001274" | "cg05382973" | "cg10451502" | "cg26592319" |
| "cg12502223" | "cg16821345" | "cg14863124" | "cg00492691" | "cg06976222" | "cg01334432" |

TABLE 12-continued

| \multicolumn{6}{c|}{Variables selected by LASSO/elasticnet for Mg deficiency in BS} |

| | | | | | |
|---|---|---|---|---|---|
| "cg04891094" | "cg24396686" | "cg13992360" | "cg11343713" | "cg02074074" | "cg17446661" |
| "cg01793068" | "cg06432889" | "cg17313709" | "cg14185463" | "cg09272948" | "cg07070882" |

For Mg insufficiency, LASSO/elasticnet regression fits pick 160 5-mC sites using approach 1.

TABLE 13

Variables selected by LASSO/elasticnet for Mg deficiency in BS

| | | | | |
|---|---|---|---|---|
| "cg09936824" | "cg05660803" | "cg12600069" | "cg27649897" | "cg10503473" |
| "cg24216889" | "cg17105557" | "cg02460812" | "cg07554408" | "cg24135151" |
| "cg18233497" | "cg25600049" | "cg02027123" | "cg19490001" | "cg18956714" |
| "cg24576206" | "cg21875096" | "cg14503881" | "cg22328746" | "cg16621176" |
| "cg16602850" | "cg19405842" | "cg16722435" | "cg05382973" | "cg13503928" |
| "cg04426842" | "cg10581837" | "cg09182447" | "cg10231801" | "cg24025119" |
| "cg07522508" | "cg01152729" | "cg06917858" | "cg03301025" | "cg24396686" |
| "cg18096764" | "cg12463089" | "cg01660034" | "cg11466504" | "cg09307977" |
| "cg00946712" | "cg03007338" | "cg05241538" | "cg06131046" | "cg19980575" |
| "cg07686023" | "cg10909141" | "cg08759026" | "cg11368392" | "cg10855773" |
| "cg21593628" | "cg20360416" | "cg04896013" | "cg18326365" | "cg12475128" |
| "cg16398761" | "cg17420619" | "cg09949366" | "cg25789861" | "cg10062141" |
| "cg14759277" | "cg05417607" | "cg07908870" | "cg27483474" | "cg19206146" |
| "cg19987296" | "cg16055294" | "cg00134295" | "cg06108900" | "cg10420854" |
| "cg07081465" | "cg05351998" | "cg02928110" | "cg27118849" | "cg19594772" |
| "cg25117895" | "cg12477050" | "cg13431573" | "cg14880655" | "cg07425005" |
| "cg25276640" | "cg10491546" | "cg11485283" | "cg21178711" | "cg02779870" |
| "cg09962477" | "cg23997664" | "cg04094346" | "cg21130113" | "cg11534242" |
| "cg15486846" | "cg15715690" | "cg10983873" | "cg16152741" | "cg26592319" |
| "cg03538548" | "cg01758805" | "cg27156529" | "cg22721434" | "cg22673476" |
| "cg16821345" | "cg05315240" | "cg23027329" | "cg25089903" | "cg10848640" |
| "cg21956258" | "cg18777236" | "cg07009570" | "cg07070882" | "cg24611214" |
| "cg24354380" | "cg25794707" | "cg16477259" | "cg21656199" | "cg14681115" |
| "cg00492691" | "cg07399846" | "cg01076051" | "cg25826576" | "cg03374632" |
| "cg01043567" | "cg13233725" | "cg08440418" | "cg24687894" | "cg20002846" |
| "cg16503559" | "cg24013810" | "cg11495399" | "cg16484858" | "cg08937612" |
| "cg23902439" | "cg19926480" | "cg23664783" | "cg05071577" | "cg20051696" |
| "cg09223811" | "cg02013841" | "cg05064673" | "cg18477635" | "cg18049571" |
| "cg02074074" | "cg27617214" | "cg06868100" | "cg18848965" | "cg24202485" |
| "cg22287711" | "cg27658811" | "cg08822689" | "cg03901836" | "cg01095103" |
| "cg15185001" | "cg02556675" | "cg19440992" | "cg18670278" | "cg03234777" |
| "cg24351671" | "cg09445162" | "cg04645444" | "cg21244116" | "cg25225632" |

For Mg deficiency, LASSO/elasticnet regression fits pick 43 sites using approach 2.

TABLE 14

Variables selected by LASSO/elasticnet for Mg deficiency in BS

| | | | | | |
|---|---|---|---|---|---|
| "cg18910313" | "cg01892689" | "cg18016565" | "cg24375627" | "cg21494343" | "cg16484042" |
| "cg15916246" | "cg16978871" | "cg03170318" | "cg08690634" | "cg19066691" | "cg01016169" |
| "cg14436032" | "cg19406106" | "cg23255151" | "cg15740518" | "cg13867683" | "cg08878802" |
| "cg01278712" | "cg10660498" | "cg16085056" | "cg15711208" | "cg08198851" | "cg25962755" |
| "cg06844749" | "cg13865595" | "cg14595922" | "cg19109677" | "cg19615147" | "cg20808227" |
| "cg13192508" | "cg16106313" | "cg16395700" | "cg14480619" | "cg26510597" | "cg26553263" |
| "cg19591710" | "cg25041035" | "cg00444883" | "cg04464650" | | |
| "cg05347567" | "cg15522298" | "cg13877657" | | | |

For Mg insufficiency, LASSO/elasticnet regression fits pick 253 sites using approach 2.

TABLE 15

Variables selected by LASSO/elasticnet for Mg deficiency in BS

| | | | | | |
|---|---|---|---|---|---|
| "cg01654446" | "cg13323097" | "cg12461252" | "cg10055621" | "cg25034625" | "cg21480996" |
| "cg07912402" | "cg26608883" | "cg13272280" | "cg09603594" | "cg08570492" | "cg02563636" |
| "cg04353660" | "cg15269754" | "cg11962515" | "cg00514268" | "cg18308359" | "cg12566078" |
| "cg15916628" | "cg10712573" | "cg00264384" | "cg07537978" | "cg11705931" | "cg26722858" |
| "cg22662556" | "cg08520660" | "cg08159120" | "cg19301992" | "cg12269394" | "cg05285687" |

TABLE 15-continued

Variables selected by LASSO/elasticnet for Mg deficiency in BS

| | | | | | |
|---|---|---|---|---|---|
| "cg25545088" | "cg26291276" | "cg22524174" | "cg16350010" | "cg06981948" | "cg02847344" |
| "cg05083647" | "cg02942142" | "cg16495809" | "cg23012185" | "cg09886858" | "cg00873704" |
| "cg24999679" | "cg07146974" | "cg13626842" | "cg19504661" | "cg10061496" | "cg16655404" |
| "cg26744387" | "cg06005396" | "cg03859915" | "cg19752094" | "cg11909137" | "cg10308906" |
| "cg22120017" | "cg08170757" | "cg27145495" | "cg25732732" | "cg21622381" | "cg04231467" |
| "cg17431746" | "cg21041792" | "cg00997174" | "cg07817409" | "cg05988267" | "cg10732215" |
| "cg25178784" | "cg01157169" | "cg24659093" | "cg11967835" | "cg23377495" | "cg10679147" |
| "cg10498926" | "cg24287362" | "cg17492717" | "cg00700455" | "cg22455392" | "cg09142260" |
| "cg22492435" | "cg01884445" | "cg26539873" | "cg07763398" | "cg10273666" | "cg26142604" |
| "cg09044656" | "cg17753476" | "cg18048027" | "cg06217399" | "cg21809040" | "cg16136290" |
| "cg08506990" | "cg02941697" | "cg06482534" | "cg01280589" | "cg01851573" | "cg05362892" |
| "cg26125864" | "cg01748805" | "cg21057880" | "cg07283630" | "cg19560579" | "cg10680854" |
| "cg06246435" | "cg18315249" | "cg20393707" | "cg04379126" | "cg15711208" | "cg05347173" |
| "cg01640958" | "cg25498045" | "cg08934843" | "cg26045331" | "cg07604566" | "cg23352145" |
| "cg01458041" | "cg19592898" | "cg27506098" | "cg10130703" | "cg08191469" | "cg25912173" |
| "cg19667913" | "cg07708947" | "cg26369996" | "cg26352440" | "cg23175573" | "cg04344303" |
| "cg19021236" | "cg26903218" | "cg24406391" | "cg12406651" | "cg08379517" | "cg27488807" |
| "cg00640253" | "cg18998321" | "cg06045761" | "cg17547883" | "cg07581775" | "cg08706575" |
| "cg03826480" | "cg00908117" | "cg18304936" | "cg02341645" | "cg20963002" | "cg07698266" |
| "cg01705888" | "cg01456285" | "cg04861494" | "cg20984904" | "cg21710569" | "cg23564460" |
| "cg09055507" | "cg02339032" | "cg04088074" | "cg24073042" | "cg19260922" | "cg13259063" |
| "cg07508452" | "cg18964630" | "cg23262555" | "cg00181497" | "cg21198880" | "cg09450352" |
| "cg16181135" | "cg13988329" | "cg06626140" | "cg20659752" | "cg15328328" | "cg07015412" |
| "cg22715072" | "cg22914616" | "cg03408135" | "cg17239714" | "cg23757365" | "cg11304573" |
| "cg11231279" | "cg27115113" | "cg06647930" | "cg22775776" | "cg18981248" | "cg03080336" |
| "cg11775846" | "cg14132288" | "cg12319618" | "cg16896144" | "cg07973125" | "cg14451730" |
| "cg22920609" | "cg17760895" | "cg18867708" | "cg19051504" | "cg22511432" | "cg25623271" |
| "cg20911168" | "cg05141695" | "cg05356308" | "cg18930100" | "cg26589591" | "cg17304878" |
| "cg09041485" | "cg20252903" | "cg22736872" | "cg24184350" | "cg22869660" | "cg27326823" |
| "cg23321841" | "cg11918124" | "cg13831860" | "cg26832999" | "cg17601661" | "cg27296963" |
| "cg01443408" | "cg05980922" | "cg27413396" | "cg27383534" | "cg26127187" | "cg14999518" |
| "cg05314679" | "cg10713715" | "cg13865595" | "cg18523042" | "cg02992951" | "cg27266060" |
| "cg26990667" | "cg19916364" | "cg19335381" | "cg00594167" | "cg04260065" | "cg06788751" |
| "cg19486702" | "cg06773584" | "cg11633280" | "cg02222170" | "cg02658969" | "cg21947394" |
| "cg21085679" | "cg12144374" | "cg17887537" | "cg25687573" | "cg16258229" | "cg20405742" |
| "cg14526241" | "cg22699815" | "cg26912485" | "cg06190612" | "cg22547226" | "cg26667659" |
| "cg10673318" | "cg04272994" | "cg19701205" | "cg22536351" | "cg21293943" | "cg03356877" |
| "cg26954056" | | | | | |

For Mg deficiency, LASSO/elasticnet regression fits pick 71 5-hmC sites using approach 1.

TABLE 16

Variables selected by LASSO/elasticnet for Mg deficiency in BS

| | | | | | |
|---|---|---|---|---|---|
| "cg19942593" | "cg25883327" | "cg25779653" | "cg25506514" | "cg08688393" | "cg10129485" |
| "cg16880176" | "cg17980786" | "cg01783579" | "cg15768413" | "cg02468643" | "cg00162806" |
| "cg02272814" | "cg10997203" | "cg09443697" | "cg19277119" | "cg26916871" | "cg24705717" |
| "cg07461432" | "cg18414025" | "cg19836423" | "cg08752155" | "cg17235953" | "cg01211097" |
| "cg04124858" | "cg13306164" | "cg06600135" | "cg03383975" | "cg19451311" | "cg16075006" |
| "cg05559978" | "cg06007434" | "cg17787108" | "cg19404184" | "cg10940515" | "cg11514839" |
| "cg16735465" | "cg03451760" | "cg19188464" | "cg26517176" | "cg05852416" | "cg24613956" |
| "cg16646600" | "cg23703711" | "cg14725164" | "cg09313831" | "cg16371860" | "cg07565441" |
| "cg22979531" | "cg10641986" | "cg07785314" | "cg19872463" | "cg08316054" | "cg03345059" |
| "cg07513561" | "cg07814712" | "cg00685863" | "cg07734259" | "cg03092609" | "cg08288894" |
| "cg11824316" | "cg21627706" | "cg15961993" | "cg09600529" | "cg17066470" | "cg22571271" |
| "cg04202957" | "cg26390078" | "cg25763709" | "cg06331446" | "cg00552805" | |

For Mg insufficiency, LASSO/elasticnet regression fits pick 54 sites using approach 1.

TABLE 17

Variables selected by LASSO/elasticnet for Mg deficiency in BS

| | | | | | |
|---|---|---|---|---|---|
| "cg20678128" | "cg05595943" | "cg01783579" | "cg11514839" | "cg19702274" | "cg02272814" |
| "cg09078754" | "cg07461432" | "cg05138062" | "cg11528570" | "cg06858541" | "cg08752155" |
| "cg14725164" | "cg00446065" | "cg09718640" | "cg06830769" | "cg27649897" | "cg03381216" |
| "cg17819702" | "cg08790584" | "cg19993845" | "cg13432294" | "cg03345059" | "cg05351998" |
| "cg00968310" | "cg02804655" | "cg19404184" | "cg00666845" | "cg24987590" | "cg17934130" |
| "cg18936620" | "cg25257051" | "cg19783306" | "cg02858997" | "cg22689016" | "cg18610423" |
| "cg01211109" | "cg02484886" | "cg02017534" | "cg04144515" | "cg05365607" | "cg16195970" |

TABLE 17-continued

Variables selected by LASSO/elasticnet for Mg deficiency in BS

| | | | | | |
|---|---|---|---|---|---|
| "cg04426842" | "cg15732149" | "cg19277119" | "cg23657865" | "cg07439208" | "cg26278666" |
| "cg18634848" | "cg13753657" | "cg08456112" | "cg06894069" | "cg21099767" | "cg21884589" |

For Mg deficiency, LASSO/elasticnet regression fits pick 54 sites using approach 2.

TABLE 18

Variables selected by LASSO/elasticnet for Mg deficiency in BS

| | | | | | |
|---|---|---|---|---|---|
| "cg01672172" | "cg15965578" | "cg02812510" | "cg24197051" | "cg07869659" | "cg24330553" |
| "cg08984686" | "cg11997359" | "cg03924111" | "cg14160449" | "cg03539876" | "cg17572903" |
| "cg02968715" | "cg10342304" | "cg25921358" | "cg03235871" | "cg09664812" | "cg00574206" |
| "cg24970361" | "cg14810004" | "cg20153590" | "cg02383399" | "cg07119028" | "cg08411738" |
| "cg20149871" | "cg07574385" | "cg17251609" | "cg12670862" | "cg05962733" | "cg00577164" |
| "cg24022829" | "cg01628181" | "cg02722511" | "cg08216099" | "cg23785114" | "cg22095253" |
| "cg17528662" | "cg25130134" | "cg07613047" | "cg05135521" | "cg07976328" | "cg16385758" |
| "cg14859088" | "cg04275362" | "cg07230522" | "cg16642721" | "cg14991358" | "cg08558495" |
| "cg20299810" | "cg05244236" | "cg17767224" | "cg13877657" | "cg02423930" | "cg25005374" |

For Mg insufficiency, LASSO/elasticnet regression fits pick 130 sites using approach 2.

TABLE 19

Variables selected by LASSO/elasticnet for Mg deficiency in BS

| | | | | | |
|---|---|---|---|---|---|
| "cg12546785" | "cg20558790" | "cg23050436" | "cg23262555" | "cg27070952" | "cg23043438" |
| "cg24955156" | "cg27141863" | "cg07139928" | "cg21057217" | "cg24034568" | "cg13323097" |
| "cg05780543" | "cg25349350" | "cg26747293" | "cg02085507" | "cg26644049" | "cg18833720" |
| "cg01400516" | "cg23361930" | "cg23115387" | "cg05372730" | "cg08463929" | "cg13673137" |
| "cg16616370" | "cg08327708" | "cg04762756" | "cg18581781" | "cg10273666" | "cg18372013" |
| "cg05168062" | "cg03065601" | "cg01612232" | "cg25965355" | "cg11727826" | "cg27646850" |
| "cg00036272" | "cg14322298" | "cg19495079" | "cg01814149" | "cg06839650" | "cg17137671" |
| "cg19504736" | "cg26753307" | "cg24702286" | "cg26196162" | "cg19703425" | "cg01808547" |
| "cg00203160" | "cg14375890" | "cg14983108" | "cg16829297" | "cg09312590" | "cg04276750" |
| "cg23169762" | "cg03521625" | "cg08841098" | "cg02128882" | "cg17178489" | "cg11008674" |
| "cg22832808" | "cg02961620" | "cg10720040" | "cg25151806" | "cg18156003" | "cg27607805" |
| "cg05285687" | "cg14796889" | "cg12579764" | "cg03071553" | "cg10739136" | "cg17409731" |
| "cg02339369" | "cg21852208" | "cg25182665" | "cg18270378" | "cg13164309" | "cg26596734" |
| "cg05847038" | "cg11369564" | "cg10142237" | "cg07442244" | "cg12031217" | "cg04548032" |
| "cg25025983" | "cg23651872" | "cg07943346" | "cg23012185" | "cg14626660" | "cg23757365" |
| "cg27371264" | "cg09150559" | "cg11333968" | "cg23695209" | "cg16923826" | "cg20537611" |
| "cg27241190" | "cg00597107" | "cg06177599" | "cg25362525" | "cg04396185" | "cg07912402" |
| "cg11621211" | "cg02235659" | "cg27030854" | "cg16554615" | "cg10538654" | "cg15548346" |
| "cg06483661" | "cg12638844" | "cg14309111" | "cg23894443" | "cg02362409" | "cg24141156" |
| "cg17382986" | "cg01972688" | "cg05324991" | "cg12317021" | "cg23281384" | "cg13776199" |
| "cg17796982" | "cg02646091" | "cg07502730" | "cg00851782" | "cg16018314" | "cg13168333" |
| "cg03940024" | "cg04754212" | "cg17602884" | "cg18122443" | | |

Table 20 presents the BS methylation markers selected by LASSO at lambda value that minimizes the mean squared error rate for continuous magnesium status.

TABLE 20

Variables selected by LASSO

| Name | Beta | OR |
|---|---|---|
| cg05019905 | 167.198677 | 4.106416e+72 |
| cg00924527 | −10.087378 | 4.160000e−05 |
| cg15021089 | −140.149493 | 0.000000e+00 |
| cg12800781 | −4.044777 | 1.751360e−02 |

Table 21 presents the BS methylation markers selected by Elasticnet with alpha=0.25 at lambda value that minimizes the mean squared error rate for continuous magnesium status.

TABLE 21

Variables selected by Elasticnet fit alpha = 0.25

| Name | Beta | OR |
|---|---|---|
| cg05019905 | 122.144402 | 1.113371e+53 |
| cg11840205 | 2.564487 | 1.299399e+01 |
| cg15210809 | −9.464701 | 7.750000e−05 |
| cg00924527 | −15.353084 | 2.000000e−07 |
| cg15021089 | −85.633748 | 0.000000e+00 |
| cg12800781 | −11.881832 | 6.900000e−06 |

Table 22 presents the BS methylation markers selected by Elasticnet with alpha=0.5 at lambda value that minimizes the mean squared error rate for continuous magnesium status.

TABLE 22

| Variables selected by Elasticnet fit alpha = 0.5 | | |
|---|---|---|
| Name | Beta | OR |
| cg05019905 | 129.343026 | 1.489232e+56 |
| cg15210809 | −1.401056 | 2.463368e−01 |
| cg00924527 | −10.158863 | 3.870000e−05 |
| cg15021089 | −104.449342 | 0.000000e+00 |
| cg12800781 | −7.871308 | 3.815000e−04 |

Table 23 presents the BS methylation markers selected by Elasticnet with alpha=0.75 at lambda value that minimizes the mean squared error rate for continuous magnesium status.

TABLE 23

| Variables selected by Elasticnet fit alpha = 0.75 | | |
|---|---|---|
| Name | Beta | OR |
| cg05019905 | 151.731653 | 7.874437e+65 |
| cg00924527 | −10.338433 | 3.240000e−05 |
| cg15021089 | −125.496642 | 0.000000e+00 |
| cg12800781 | −6.063569 | 2.326100e−03 |

Table 24 presents the BS methylation markers selected by LASSO at lambda value that minimizes the mean square error rate for continuous magnesium status.

TABLE 23

| Variables selected by LASSO fit at lambda.min | | |
|---|---|---|
| Name | Beta | OR |
| cg08828389 | 138.865506 | 2.034806e+60 |
| cg05995260 | −135.501610 | 0.000000e+00 |
| cg04778331 | 1183.296218 | Inf |
| cg17431860 | 641.914211 | 6.022818e+278 |
| cg09823095 | 12.929707 | 4.123829e+05 |
| cg06510234 | −7.448462 | 5.823000e−04 |
| cg12418357 | 121.079716 | 3.839303e+52 |
| cg04530860 | 351.014430 | 2.777347e+152 |
| cg02073796 | −8.946129 | 1.302000e−04 |
| cg07937803 | −24.130111 | 0.000000e+00 |
| cg08202165 | 50.496900 | 8.521679e+21 |
| cg22798756 | 48.704348 | 1.419155e+21 |
| cg24210818 | −26.845604 | 0.000000e+00 |
| cg06045761 | 32.657780 | 1.524381e+14 |
| cg02916173 | −29.488199 | 0.000000e+00 |
| cg19434718 | 16.827155 | 2.032080e+07 |
| cg03043243 | 3.446144 | 3.137916e+01 |

Table 25 presents the BS methylation markers selected by Elasticnet with alpha=0.25 at lambda value that minimizes the mean squared error rate for continuous magnesium status.

TABLE 24

| Variables selected by Elasticnet fit alpha = 0.25 | | |
|---|---|---|
| Name | Beta | OR |
| cg08828389 | 115.1918321 | 1.064577e+50 |
| cg05995260 | −100.9931990 | 0.000000e+00 |
| cg04778331 | 707.2274189 | 1.396257e+307 |
| cg17431860 | 385.7032569 | 3.226979e+167 |
| cg09823095 | 68.5944187 | 6.168471e+29 |
| cg06510234 | −5.7014958 | 3.341000e−03 |
| cg12418357 | 333.4379260 | 6.460280e+144 |
| cg04530860 | 240.3691265 | 2.460284e+104 |

TABLE 24-continued

| Variables selected by Elasticnet fit alpha = 0.25 | | |
|---|---|---|
| Name | Beta | OR |
| cg02073796 | −3.6532932 | 2.590570e−02 |
| cg19400873 | 0.3081523 | 1.360908e+00 |
| cg07937803 | −8.7811010 | 1.536000e−04 |
| cg15711208 | −0.1705206 | 8.432257e−01 |
| cg08202165 | 22.0573539 | 3.796532e+09 |
| cg08520660 | −4.0741794 | 1.700620e−02 |
| cg22798756 | 18.4489354 | 1.028658e+08 |
| cg24210818 | −15.8078627 | 1.000000e−07 |
| cg19615147 | 7.2197536 | 1.366152e+03 |
| cg06045761 | 18.9400187 | 1.680914e+08 |
| cg25767906 | 5.8479146 | 3.465110e+02 |
| cg02916173 | −31.9175271 | 0.000000e+00 |
| cg17373759 | 0.1197168 | 1.127177e+00 |
| cg20405742 | −0.9694672 | 3.792851e−01 |
| cg19531475 | −8.1667245 | 2.839000e−04 |
| cg19434718 | 10.5741498 | 3.911064e+04 |
| cg03043243 | 2.3987769 | 1.100970e+01 |
| cg13175850 | −0.1669210 | 8.437315e−01 |

Table 26 presents the BS methylation markers selected by Elasticnet with alpha=0.5 at lambda value that minimizes the mean squared error rate for continuous magnesium status.

TABLE 25

| Variables selected by Elasticnet fit alpha = 0.5 | | |
|---|---|---|
| Name | Beta | OR |
| cg05995260 | −98.671875 | 0.000000e+00 |
| cg04778331 | 743.208587 | Inf |
| cg17431860 | 314.640730 | 4.433358e+136 |
| cg09823095 | 3.468884 | 3.210090e+01 |
| cg12418357 | 60.600049 | 2.080975e+26 |
| cg04530860 | 186.419395 | 9.139333e+80 |
| cg02073796 | −3.932358 | 1.959740e−02 |
| cg07937803 | −6.139188 | 2.156700e−03 |
| cg08202165 | 32.846534 | 1.841063e+14 |
| cg22798756 | 14.758575 | 2.567838e+06 |
| cg24210818 | −13.940851 | 9.000000e−07 |
| cg19615147 | 3.267453 | 2.624441e+01 |
| cg06045761 | 22.445195 | 5.595311e+09 |
| cg25767906 | 2.907708 | 1.831477e+01 |
| cg02916173 | −28.512119 | 0.000000e+00 |
| cg19434718 | 9.221180 | 1.010899e+04 |
| cg03043243 | 2.337433 | 1.035462e+01 |

Table 27 presents the BS methylation markers selected by Elasticnet with alpha=0.75 at lambda value that minimizes the mean squared error rate for continuous magnesium status.

TABLE 26

| Variables selected by Elasticnet fit alpha = 0.75 | | |
|---|---|---|
| Name | Beta | OR |
| cg08828389 | 210.851913 | 3.730974e+91 |
| cg05995260 | −141.564206 | 0.000000e+00 |
| cg04778331 | 1143.339735 | Inf |
| cg17431860 | 608.753224 | 2.388724e+264 |
| cg09823095 | 38.430211 | 4.898108e+16 |
| cg06510234 | −9.172619 | 1.038000e−04 |
| cg12418357 | 262.019506 | 6.217640e+113 |
| cg04530860 | 347.116610 | 5.634148e+150 |
| cg02073796 | −8.035824 | 3.237000e−04 |
| cg07937803 | −21.915744 | 0.000000e+00 |
| cg08202165 | 43.975895 | 1.254551e+19 |
| cg22798756 | 42.012923 | 1.761897e+18 |
| cg24210818 | −25.701806 | 0.000000e+00 |

TABLE 26-continued

Variables selected by Elasticnet fit alpha = 0.75

| Name | Beta | OR |
| --- | --- | --- |
| cg06045761 | 30.178299 | 1.277229e+13 |
| cg25767906 | 1.962401 | 7.116395e+00 |
| cg02916173 | -35.188482 | 0.000000e+00 |
| cg19434718 | 17.253811 | 3.113401e+07 |
| cg03043243 | 3.472041 | 3.220240e+01 |

Table 28 presents the 5-mC methylation markers selected by LASSO at lambda value that minimizes the mean squared error rate for continuous magnesium.

TABLE 27

Variables selected by LASSO

| Name | Beta | OR |
| --- | --- | --- |
| cg07121807 | 6.028887 | 415.25252 |
| cg08001123 | -32.979351 | 0.00000 |
| cg04426842 | -17.210661 | 0.00000 |
| cg24687894 | 7.094252 | 1205.02029 |
| cg06392664 | 4.201440 | 66.78244 |

Table 29 presents the 5-mC methylation markers selected by Elasticnet with alpha=0.25 at lambda value that minimizes the mean squared error rate for continuous

TABLE 28

Variables selected by Elasticnet fit alpha = 0.25

| Name | Beta | OR |
| --- | --- | --- |
| cg07121807 | 3.731745 | 41.7519114 |
| cg08001123 | -20.288714 | 0.0000000 |
| cg03889299 | 1.924902 | 6.8544797 |
| cg10983873 | -3.046954 | 0.0475034 |
| cg04426842 | -9.041472 | 0.0001184 |
| cg24687894 | 3.353182 | 28.5935612 |
| cg06382664 | 3.937142 | 51.2718752 |

Table 30 presents the 5-mC methylation markers selected by Elasticnet with alpha=0.5 at lambda value that minimizes the mean squared error rate for continuous magnesium.

TABLE 29

Variables selected by Elasticnet fit alpha = 0.5

| Name | Beta | OR |
| --- | --- | --- |
| cg07121807 | 1.710080 | 5.5294042 |
| cg08001123 | -17.752705 | 0.0000000 |
| cg04426842 | -10.386653 | 0.0000308 |
| cg24687894 | 2.477333 | 11.9094608 |
| cg06382664 | 2.580519 | 13.2039880 |

Table 31 presents the 5-mC methylation markers selected by Elasticnet with alpha=0.75 at lambda value that minimizes the mean squared error rate for continuous magnesium.

TABLE 30

Variables selected by Elasticnet fit alpha = 0.75

| Name | Beta | OR |
| --- | --- | --- |
| cg07121807 | 5.839709 | 343.6791269 |
| cg08001123 | -31.113077 | 0.0000000 |

TABLE 30-continued

Variables selected by Elasticnet fit alpha = 0.75

| Name | Beta | OR |
| --- | --- | --- |
| cg04426842 | -15.634694 | 0.0000002 |
| cg24687894 | 6.301561 | 545.4228447 |
| cg06382664 | 4.475123 | 87.8053585 |

Table 32 presents the 5-mC methylation markers selected by LASSO at lambda value that minimizes the mean squared error rate for continuous magnesium.

TABLE 31

Variables selected by LASSO

| Name | Beta | OR |
| --- | --- | --- |
| cg16978871 | 168.8655581 | 2.174603e+73 |
| cg26744387 | -454.0816703 | 0.000000e+00 |
| cg15577559 | 16.0920146 | 9.742561e+06 |
| cg22120017 | 425.3692651 | 5.439070e+184 |
| cg03529803 | -193.6133078 | 0.000000e+00 |
| cg16436867 | -323.2394483 | 0.000000e+00 |
| cg14258935 | -308.6214036 | 0.000000e+00 |
| cg22492435 | -32.5284342 | 0.000000e+00 |
| cg02073796 | -2.3424258 | 9.609420e-02 |
| cg15989720 | 3.2959008 | 2.700173e+01 |
| cg13226135 | 1.7299539 | 5.640394e+00 |
| cg15740518 | 97.0888704 | 1.462718e+42 |
| cg23172059 | 6.2167359 | 5.010650e+02 |
| cg15711208 | -34.0070716 | 0.000000e+00 |
| cg08202165 | 32.2456398 | 1.009492e+14 |
| cg08520660 | -18.5568863 | 0.000000e+00 |
| cg03238677 | 6.0886201 | 4.408127e+02 |
| cg19615147 | 53.7861012 | 2.285635e+23 |
| cg06045761 | 17.9116196 | 6.010597e+07 |
| cg13192508 | 4.4040006 | 8.177737e+01 |
| cg22043275 | -5.8273224 | 2.946000e+03 |
| cg12026858 | 10.7278595 | 4.560896e+04 |
| cg24520234 | -14.0790374 | 8.000000e-07 |
| cg25767906 | 1.1096137 | 3.033186e+00 |
| cg20405742 | -15.8009896 | 1.000000e+07 |
| cg12544293 | 0.0563505 | 1.057968e+00 |
| cg21801549 | 10.1838319 | 2.647171e+04 |
| cg12165250 | -42.4279469 | 0.000000e+00 |
| cg10413151 | 9.4485487 | 1.268974e+04 |
| cg05031435 | -53.2325187 | 0.000000e+00 |
| cg25143609 | 3.4701042 | 3.214009e+01 |
| cg17542650 | 2.1587528 | 8.660330e+00 |
| cg05525594 | 4.4426723 | 8.500179e+01 |
| cg15522298 | 0.9449790 | 2.572759e+00 |
| cg21302538 | -21.4355254 | 0.000000e+00 |
| cg11757337 | -0.8649319 | 4.210802e-01 |
| cg05444524 | -6.1084300 | 2.224000e-03 |

Table 33 presents the 5-mC methylation markers selected by Elasticnet with alpha=0.25 at lambda value that minimizes the mean squared error rate for continuous magnesium.

TABLE 32

Variables selected by Elasticnet fit alpha = 0.25

| Name | Beta | OR |
| --- | --- | --- |
| cg16978871 | 153.6391738 | 5.304512e+66 |
| cg06026520 | 2.3928664 | 1.094482e+01 |
| cg26744387 | -214.8360175 | 0.000000e+00 |
| cg05995260 | -24.5952038 | 0.000000e+00 |
| cg22120017 | 274.0051372 | 9.975142e+118 |
| cg13323097 | -142.0225249 | 0.000000e+00 |
| cg23029526 | 116.4674538 | 3.812172e+50 |
| cg03529803 | -138.3640631 | 0.000000e+00 |

TABLE 32-continued

Variables selected by Elasticnet fit alpha = 0.25

| Name | Beta | OR |
|---|---|---|
| cg16436867 | −143.7549508 | 0.000000e+00 |
| cg22280238 | 67.1420760 | 1.443554e+29 |
| cg19066691 | 7.7304470 | 2.276620e+03 |
| cg14258935 | −77.7791875 | 0.000000e+00 |
| cg22492435 | −15.2793723 | 2.000000e−07 |
| cg02073796 | −1.9894817 | 1.367663e−01 |
| cg15989720 | 1.4248432 | 4.157206e+00 |
| cg13226135 | 3.8225455 | 4.572044e+01 |
| cg15740518 | 43.0302025 | 4.872810e+18 |
| cg23172059 | 8.6536099 | 5.730797e+03 |
| cg00781388 | −3.1187924 | 4.421050e−02 |
| cg15711208 | −30.5642598 | 0.000000e+00 |
| cg04312620 | −0.3283286 | 7.201264e−01 |
| cg08202165 | 17.8940211 | 5.905744e+07 |
| cg08520660 | −10.4024631 | 3.040000e−05 |
| cg03238677 | 2.1111501 | 8.257733e+00 |
| cg06528228 | −3.0062450 | 4.947710e−02 |
| cg19615147 | 29.8630053 | 9.318337e+12 |
| cg06045761 | 14.7964860 | 2.667056e+06 |
| cg22676923 | −5.7299470 | 3.247200e−03 |
| cg13192508 | 6.5129613 | 6.738188e+02 |
| cg12026858 | 6.1264297 | 4.577988e+02 |
| cg24520234 | −11.9423197 | 6.500000e−06 |
| cg25767906 | 5.4487252 | 2.324616e+02 |
| cg20405742 | −7.3223499 | 6.606000e−04 |
| cg09383456 | −14.2588785 | 6.000000e−07 |
| cg21801549 | 9.4633042 | 1.287837e+04 |
| cg17753427 | −0.4919550 | 6.114299e−01 |
| cg12165250 | −21.2878781 | 0.000000e+00 |
| cg16642721 | 0.0199829 | 1.020184e+00 |
| cg11635325 | −1.6269720 | 1.965237e−01 |
| cg10413151 | 3.1638279 | 2.366100e+01 |
| cg19531475 | −16.2727070 | 1.000000e−07 |
| cg05031435 | −26.7068285 | 0.000000e+00 |
| cg15355341 | 6.3353840 | 5.641860e+02 |
| cg03043243 | 0.3733803 | 1.452637e+00 |
| cg19247001 | 81.9360640 | 3.840436e+35 |
| cg17542650 | 2.4427495 | 1.150463e+01 |
| cg05525594 | 1.8610654 | 6.430584e+00 |
| cg15522298 | 4.5193889 | 9.177950e+01 |
| cg13410153 | 0.7554803 | 2.128634e+00 |
| cg21302538 | −24.6333983 | 0.000000e+00 |
| cg11757337 | −11.3735808 | 1.150000e−05 |
| cg05444524 | −5.7626209 | 3.142900e−03 |

Table 34 presents the 5-mC methylation markers selected by Elasticnet with alpha=0.5 at lambda value that minimizes the mean squared error rate for continuous

TABLE 34

Variables selected by Elasticnet fit alpha = 0.75

| Name | Beta | OR |
|---|---|---|
| cg16978871 | 176.5659273 | 4.804055e+76 |
| cg06026520 | 0.8235186 | 2.278503e+00 |
| cg26744387 | −310.9720561 | 0.000000e+00 |
| cg22120017 | 357.4438279 | 1.720024e+155 |
| cg13323897 | −97.6926325 | 0.000000e+00 |
| cg23029526 | 00.9472404 | 2.944782e+28 |
| cg03529803 | −164.1334361 | 0.000000e+00 |
| cg16436867 | −216.0442581 | 0.000000e+00 |
| cg22280238 | 54.4268508 | 4.337914e+23 |
| cg14258935 | −147.4915193 | 0.000000e+00 |
| cg22492435 | −19.7679952 | 0.000000e+00 |
| cg02073796 | −1.8387406 | 1.590176e−01 |
| cg15989720 | 1.9796313 | 7.241521e+00 |
| cg13226135 | 4.0350752 | 5.654717e+01 |
| cg15740518 | 66.6554394 | 8.873389e+28 |
| cg23172059 | 9.9175384 | 2.028300e+04 |
| cg00781388 | −0.4737788 | 6.226450e−01 |
| cg15711208 | −35.7591629 | 0.000000e+00 |
| cg19850463 | −0.0079288 | 9.921025e−01 |

TABLE 34-continued

Variables selected by Elasticnet fit alpha = 0.75

| Name | Beta | OR |
|---|---|---|
| cg08202165 | 24.3994422 | 3.949509e+10 |
| cg08520660 | −13.6994832 | 1.100000e−06 |
| cg03238677 | 4.7777196 | 1.188381e+02 |
| cg10615147 | 41.7501915 | 1.354808e+18 |
| cg06045761 | 17.5943937 | 4.376713e+07 |
| cg22676923 | −1.5919824 | 2.035218e−01 |
| cg13192508 | 5.7547783 | 3.156955e+02 |
| cg12026858 | 7.4808056 | 1.087166e+03 |
| cg24520234 | −14.9258319 | 3.000000e−07 |
| cg25767906 | 4.5692175 | 9.646859e+01 |
| cg20405742 | −10.2489541 | 3.540000e−05 |
| cg21801549 | 10.5525170 | 3.827365e+04 |
| cg12165250 | −30.5918328 | 0.000000e+00 |
| cg10413151 | 4.6902916 | 1.088849e+02 |
| cg19531475 | −4.4139937 | 1.210670e−02 |
| cg05031435 | −36.8859424 | 0.000000e+00 |
| cg15355341 | 0.3642230 | 1.439395e+00 |
| cg19247001 | 15.9408548 | 8.375780e+06 |
| cg17542850 | 2.5037163 | 1.222785e+01 |
| cg05523594 | 0.7784029 | 2.177991e+00 |
| cg15522298 | 4.3593168 | 7.820369e+01 |
| cg21302538 | −24.8053154 | 0.000000e+00 |
| cg11757337 | −7.8961447 | 3.722000e−04 |
| cg05444524 | −7.3638780 | 6.337000e−04 |

Table 35 presents the 5-mC methylation markers selected by Elasticnet with alpha=0.75 at lambda value that minimizes the mean squared error rate for continuous

TABLE 33

Variables selected by Elasticnet fit alpha = 0.5

| Name | Beta | OR |
|---|---|---|
| cg16978871 | 168.185669 | 1.101813e+73 |
| cg26744387 | −376.932712 | 0.000000e+00 |
| cg22120017 | 400.377142 | 7.613484e+173 |
| cg13323097 | −29.580911 | 0.000000e+00 |
| cg03529803 | −181.745902 | 0.000000e+00 |
| cg16436867 | −280.279288 | 0.000000e+00 |
| cg22280238 | 34.581507 | 1.043657e+15 |
| cg14258935 | −229.972560 | 0.000000e+00 |
| cg22492435 | −24.887309 | 0.000000e+00 |
| cg02073796 | −1.933014 | 1.447114e−01 |
| cg15989720 | 2.756013 | 1.573697e+01 |
| cg13226135 | 3.177646 | 2.399021e+01 |
| cg15740518 | 83.192548 | 1.349163e+36 |
| cg23172059 | 8.937008 | 7.608397e+03 |
| cg15711208 | −34.847537 | 0.000000e+00 |
| cg08202165 | 29.008663 | 3.965540e+12 |
| cg08520660 | −15.968992 | 1.000000e−07 |
| cg03238677 | 6.656079 | 7.774965e+02 |
| cg19615147 | 49.138812 | 2.191367e+21 |
| cg06045761 | 19.015199 | 1.812158e+08 |
| cg13192508 | 4.957573 | 1.422482e+02 |
| cg12026858 | 9.316269 | 1.111742e+04 |
| cg24520234 | −15.270334 | 2.000000e−07 |
| cg25767906 | 3.395298 | 2.982355e+01 |
| cg20405742 | −12.773773 | 2.800000e−06 |
| cg21801549 | 10.492268 | 3.603581e+04 |
| cg12165250 | −36.461723 | 0.000000e+00 |
| cg10413151 | 7.077818 | 1.185379e+03 |
| cg05031435 | −45.442638 | 0.000000e+00 |
| cg17542650 | 2.752226 | 1.567749e+01 |
| cg05525594 | 1.273569 | 3.573583e+00 |
| cg15522298 | 2.917090 | 1.848741e+01 |
| cg21302538 | −24.213658 | 0.000000e+00 |
| cg11757337 | −4.138331 | 1.594940e−02 |
| cg05444324 | −7.768477 | 4.229000e−04 |

Table 36 presents the 5-hmC methylation markers selected by LASSO at lambda value that minimizes the mean squared error rate for continuous magnesium.

TABLE 35

Variables selected by LASSO

| Name | Beta | OR |
|---|---|---|
| cg18999855 | −6.512791 | 1.484300e−03 |
| cg17980786 | −45.581059 | 0.000000e+00 |
| cg01783579 | 19.329694 | 2.481872e+08 |
| cg02272814 | 3.055827 | 2.123874e+01 |
| cg19277119 | −84.958210 | 0.000000e+00 |
| cg18414025 | −38.861833 | 0.000000e+00 |
| cg08752155 | 158.457317 | 6.563542e+68 |
| cg17235953 | 378.222471 | 1.819417e+164 |
| cg21884589 | 13.257369 | 5.722716e+05 |

Table 37 presents the 5-hmC methylation markers selected by Elasticnet with alpha=0.25 at lambda value that minimizes the mean squared error rate for continuous

TABLE 36

Variables selected by Elasticnet fit alpha = 0.25

| Name | Beta | OR |
|---|---|---|
| cg19942593 | 59.9506481 | 1.087015e+26 |
| cg25779653 | 75.4684777 | 5.964080e+32 |
| cg18999855 | −49.4331796 | 0.000000e+00 |
| cg08688393 | −10.6285860 | 2.420000e−05 |
| cg16752029 | −5.3622066 | 4.698500e−03 |
| cg16880176 | 2.9051535 | 1.826805e+01 |
| cg05559978 | −17.343271 | 0.000000e+00 |
| cg17980786 | −64.8489291 | 0.000000e+00 |
| cg01783579 | 76.8154912 | 2.293739e+33 |
| cg11514839 | 32.2543656 | 1.018340e+14 |
| cg12252979 | −1.9493353 | 1.423687e−01 |
| cg12814059 | −1.5352711 | 2.153973e−01 |
| cg16193970 | −9.1923593 | 1.018000e−04 |
| cg04426842 | 4.9648411 | 1.432858e+02 |
| cg02272814 | 10.0907890 | 2.411981e+04 |
| cg11944024 | −27.8805872 | 0.000000e+00 |
| cg10997203 | −20.4650335 | 0.000000e+00 |
| cg19277119 | −76.5182092 | 0.000000e+00 |
| cg15795515 | 0.5030806 | 1.653808e+00 |
| cg26916871 | 0.3109956 | 1.364783e+00 |
| cg24613956 | −3.6990990 | 2.474580e−02 |
| cg22571271 | 64.9045160 | 1.540542e+28 |
| cg19870668 | 107.0485910 | 3.094658e+46 |
| cg18414025 | −63.0026625 | 0.000000e+00 |
| cg08752155 | 126.7241156 | 1.085386e+55 |
| cg17235953 | 498.7505991 | 4.023769e+216 |
| cg03030098 | 19.4807725 | 2.886636e+08 |
| cg21884589 | 60.4170626 | 1.732993e+26 |

Table 38 presents the 5-hmC methylation markers selected by Elasticnet with alpha=0.5 at lambda value that minimizes the mean squared error rate for continuous

TABLE 38

Variables selected by Elasticnet fit alpha = 0.5

| Name | Beta | OR |
|---|---|---|
| cg18999855 | −50.274410 | 0.000000e+00 |
| cg08688393 | −4.679491 | 9.283700e−03 |
| cg17980786 | −64.452640 | 0.000000e+00 |
| cg01783579 | 66.118950 | 5.189140e+28 |
| cg04426842 | 2.797767 | 1.640797e+01 |
| cg02272814 | 11.764888 | 1.286548e+05 |
| cg11944024 | −5.336252 | 4.813900e−03 |
| cg19277119 | −91.884163 | 0.000000e+00 |
| cg22571271 | 42.372980 | 2.525523e+18 |
| cg19870668 | 57.928091 | 1.438302e+25 |
| cg18414025 | −67.252074 | 0.000000e+00 |
| cg08752155 | 153.334947 | 3.913104e+66 |
| cg17235953 | 557.915188 | 1.992910e+242 |

TABLE 38-continued

Variables selected by Elasticnet fit alpha = 0.5

| Name | Beta | OR |
|---|---|---|
| cg03030098 | 2.002318 | 7.406203e+00 |
| cg21884589 | 48.266700 | 9.161387e+20 |

Table 39 presents the 5-hmC methylation markers selected by Elasticnet with alpha=0.75 at lambda value that minimizes the mean squared error rate for continuous magnesium.

TABLE 37

Variables selected by Elasticnet fit alpha = 0.5

| Name | Beta | OR |
|---|---|---|
| cg18999855 | −61.708361 | 0.000000e+00 |
| cg08688393 | −2.056172 | 1.279429e−01 |
| cg17980786 | −65.464170 | 0.000000e+00 |
| cg01783579 | 65.683167 | 3.356115e+28 |
| cg04426842 | 2.258579 | 9.569480e+00 |
| cg02272814 | 14.307720 | 1.635927e+06 |
| cg19277119 | −102.434209 | 0.000000e+00 |
| cg22571271 | 47.623753 | 4.816517e+20 |
| cg19870668 | 34.276798 | 7.695279e+14 |
| cg18414025 | −75.293465 | 0.000000e+00 |
| cg08752155 | 171.928844 | 4.653161e+74 |
| cg17235953 | 637.287627 | 5.895216e+276 |
| cg21884589 | 41.600807 | 1.166812e+18 |

Table 40 presents the 5-hmC methylation markers selected by LASSO at lambda value that minimizes the mean squared error rate for continuous magnesium.

TABLE 39

Variables selected by LASSO

| Name | Beta | OR |
|---|---|---|
| cg24374538 | −26.5206555 | 0.000000e+00 |
| cg03924111 | 384.6988050 | 1.181866e+167 |
| cg06219103 | −72.9059171 | 0.000000e+00 |
| cg01331064 | −95.4872762 | 0.000000e+00 |
| cg17572983 | −29.7135139 | 0.000000e+00 |
| cg15494524 | 134.5388524 | 2.688322e+58 |
| cg01672172 | −387.4245715 | 0.000000e+00 |
| cg15740518 | −6.1086325 | 2.223606e−03 |
| cg27639644 | 149.5627707 | 9.000001e+64 |
| cg04509481 | −61.8892859 | 0.000000e+00 |
| cg15252243 | −8.3300984 | 2.411000e−04 |
| cg00175823 | 0.1041116 | 1.109724e+00 |
| cg16586442 | 96.8739100 | 1.179790e+42 |
| cg05397609 | 106.5209582 | 1.825847e+46 |
| cg25182665 | −39.8583041 | 0.000000e+00 |
| cg09728629 | −75.2506493 | 0.000000e+00 |
| cg18270174 | 255.8941701 | 1.359647e+111 |
| cg10480824 | −46.1886444 | 0.000000e+00 |
| cg23651872 | −501.0590248 | 0.000000e+00 |
| cg20399983 | 6.3128010 | 5.515878e+02 |

Table 41 presents the 5-hmC methylation markers selected by Elasticnet with alpha=0.25 at lambda value that minimizes the mean squared error rate for continuous

TABLE 40

Variables selected by Elasticnet fit alpha = 0.25

| Name | Beta | OR |
|---|---|---|
| cg24374538 | −28.509247 | 0.000000e+00 |
| cg03924111 | 247.688897 | 3.714679e+107 |

TABLE 40-continued

Variables selected by Elasticnet fit alpha = 0.25

| Name | Beta | OR |
|---|---|---|
| cg06219103 | −25.912247 | 0.000000e+00 |
| cg01331064 | −35.788300 | 0.000000e+00 |
| cg20894341 | 21.888360 | 3.206225e+09 |
| cg17572903 | −13.655918 | 1.200000e−06 |
| cg15494524 | 25.583430 | 1.290454e+11 |
| cg01672172 | −140.738371 | 0.000000e+00 |
| cg15740518 | −8.601643 | 1.838000e−04 |
| cg27639644 | 45.528992 | 5.929118e+19 |
| cg13565702 | −1.071689 | 3.424295e−01 |
| cg16044562 | −14.266913 | 6.000000e−07 |
| cg04509481 | −31.326172 | 0.000000e+00 |
| cg00175823 | 7.532584 | 1.867927e+03 |
| cg24022829 | 27.108228 | 5.928621e+11 |
| cg16586442 | 37.373413 | 1.702421e+16 |
| cg05397609 | 49.189377 | 2.305022e+21 |
| cg25182665 | −21.935949 | 0.000000e+00 |
| cg09728629 | −27.799970 | 0.000000e+00 |
| cg18270174 | 112.349530 | 0.205556e+48 |
| cg10480824 | −20.210551 | 0.000000e+00 |
| cg01093429 | 34.128650 | 6.635662e+14 |
| cg16642721 | −3.264202 | 3.827740e−02 |
| cg05244236 | 1.387170 | 4.003504e+00 |
| cg23651872 | −163.050291 | 0.000000e+00 |
| cg04562755 | 3.059624 | 2.131954e+01 |
| cg20399983 | 12.021346 | 1.662663e+05 |

Table 42 presents the 5-hmC methylation markers selected by Elasticnet with alpha=0.5 at lambda value that minimizes the mean squared error rate for continuous magnesium.

TABLE 41

Variables selected by Elasticnet fit alpha = 0.5

| Name | Beta | OR |
|---|---|---|
| cg24374538 | −33.655254 | 0.000000e+00 |
| cg03924111 | 332.534362 | 2.617210e+144 |
| cg06219103 | −33.745629 | 0.000000e+00 |
| cg01331064 | −54.299997 | 0.000000e+00 |
| cg20894341 | 18.187072 | 7.916719e+07 |
| cg17572903 | −20.249879 | 0.000000e+00 |
| cg15494524 | 55.977350 | 2.044815e+24 |
| cg01672172 | −236.721324 | 0.000000e+00 |
| cg15740518 | −9.812386 | 5.480000e−05 |
| cg27639644 | 74.936304 | 3.502865e+32 |
| cg16044562 | −2.734779 | 6.490830e−02 |
| cg04509481 | −47.209553 | 0.000000e+00 |
| cg00175823 | 7.043800 | 1.145802e+03 |
| cg24022829 | 14.340020 | 1.689630e+06 |
| cg16586442 | 49.683857 | 3.779417e+21 |
| cg05397609 | 73.347851 | 7.154298e+31 |
| cg25182665 | −31.950541 | 0.000000e+00 |
| cg09728629 | −44.607688 | 0.000000e+00 |
| cg18270174 | 174.079862 | 3.998742e+75 |
| cg10480824 | −31.126525 | 0.000000e+00 |
| cg23651872 | −275.875194 | 0.000000e+00 |
| cg20399983 | 13.478978 | 7.142428e+05 |

Table 43 presents the 5-hmC methylation markers selected by Elasticnet with alpha=0.75 at lambda value that minimizes the mean squared error rate for continuous magnesium.

TABLE 42

Variables selected by Elasticnet fit alpha = 0.75

| Name | Beta | OR |
|---|---|---|
| cg24374538 | −32.171798 | 0.000000e+00 |
| cg03924111 | 370.545965 | 8.434164e+160 |

TABLE 42-continued

Variables selected by Elasticnet fit alpha = 0.75

| Name | Beta | OR |
|---|---|---|
| cg06219103 | −48.565503 | 0.000000e+00 |
| cg01331064 | −73.913877 | 0.000000e+00 |
| cg20894341 | 2.453452 | 1.162842e+01 |
| cg17572903 | −25.138338 | 0.000000e+00 |
| cg15494524 | 95.403975 | 2.712814e+41 |
| cg01672172 | −317.082391 | 0.000000e+00 |
| cg15740518 | −8.204276 | 2.735000e−04 |
| cg27639644 | 111.607470 | 2.954665e+48 |
| cg04509481 | −56.164089 | 0.000000e+00 |
| cg00175823 | 5.079676 | 1.607221e+02 |
| cg16586442 | 71.292907 | 9.164651e+30 |
| cg05397609 | 94.473546 | 1.069891e+41 |
| cg25182665 | −36.736160 | 0.000000e+00 |
| cg09728629 | −60.992877 | 0.000000e+00 |
| cg18270174 | 221.199825 | 1.163759e+96 |
| cg10480824 | −39.192160 | 0.000000e+00 |
| cg23651872 | −389.318823 | 0.000000e+00 |
| cg20399983 | 10.780226 | 4.806096e+04 |

All publications, patents, and patent applications mentioned in this specification are herein incorporated by reference to the same extent as if each individual publication, patent, or patent application was specifically and individually indicated to be incorporated by reference, including the references set forth in the following list:

REFERENCES (1) Tong G M, Rude R K. Magnesium deficiency in critical illness. *J Intensive Care Med* 2005; 20:3-17.

(2) Waters R S, Fernholz K, Bryden N A, Anderson R A. Intravenous magnesium sulfate with and without EDTA as a magnesium load test—is magnesium deficiency widespread? *Biol Trace Elem Res* 2008; 124:243-250.

(3) Ervin R B, Wang C Y, Wright J D, Kennedy-Stephenson J. Dietary intake of selected minerals for the United States population: 1999-2000. *Adv Data* 2004;1-5.

(4) Chen G C, Pang Z, Liu Q F. Magnesium intake and risk of colorectal cancer: a meta-analysis of prospective studies. *Eur J Clin Nutr* 2012; 66:1182-1186.

(5) Wark P A, Lau R, Norat T, Kampman E. Magnesium intake and colorectal tumor risk: a case-control study and meta-analysis. *Am J Clin Nutr* 2012; 96:622-631.

(6) Qu X, Jin F, Hao Y et al. Nonlinear association between magnesium intake and the risk of colorectal cancer. *Eur J Gastroenterol Hepatol* 2013; 25:309-318.

(7) Paolisso G, Sgambato S, Gambardella A et al. Daily magnesium supplements improve glucose handling in elderly subjects. *Am J Clin Nutr* 1992; 55:1161-1167.

(8) Paolisso G, Sgambato S, Pizza G, Passariello N, Varricchio M, D'Onofrio F. Improved insulin response and action by chronic magnesium administration in aged NIDDM subjects. *Diabetes Care* 1989; 12:265-269.

(9) Sjogren A, Floren C H, Nilsson A. Oral administration of magnesium hydroxide to subjects with insulin-dependent diabetes mellitus: effects on magnesium and potassium levels and on insulin requirements. *Magnesium* 1988; 7:117-122.

(10) Fung T T, Manson J E, Solomon C G, Liu S, Willett W C, Hu F B. The association between magnesium intake and fasting insulin concentration in healthy middle-aged women. *J Am Coll Nutr* 2003; 22:533-538.

(11) Song Y, Manson J E, Buring J E, Liu S. Dietary magnesium intake in relation to plasma insulin levels and risk of type 2 diabetes in women. *Diabetes Care* 2004; 27:59-65.

(12) Guerrero-Romero F, Tamez-Perez H E, Gonzalez-Gonzalez G et al. Oral magnesium supplementation improves insulin sensitivity in non-diabetic subjects with insulin resistance. A double-blind placebo-controlled randomized trial. *Diabetes Metab* 2004; 30:253-258.

(13) Mooren F C, Kruger K, Volker K, Golf S W, Wadepuhl M, Kraus A. Oral magnesium supplementation reduces insulin resistance in non-diabetic subjects—a double-blind, placebo-controlled, randomized trial. *Diabetes Obes Metab* 2011; 13:281-284.

(14) Chacko S A, Sul J, Song Y et al. Magnesium supplementation, metabolic and inflammatory markers, and global genomic and proteomic profiling: a randomized, double-blind, controlled, crossover trial in overweight individuals. *Am J Clin Nutr* 2011; 93:463-473.

(15) Song Y, He K, Levitan E B, Manson J E, Liu S. Effects of oral magnesium supplementation on glycaemic control in Type 2 diabetes: a meta-analysis of randomized double-blind controlled trials. *Diabet Med* 2006; 23:1050-1056.

(16) Champagne C M. Magnesium in hypertension, cardiovascular disease, metabolic syndrome, and other conditions: a review. *Nutr Clin Pract* 2008; 23:142-151.

(17) He K, Liu K, Daviglus M L et al. Magnesium intake and incidence of metabolic syndrome among young adults. *Circulation* 2006; 113:1675-1682.

(18) He K, Song Y, Belin R J, Chen Y. Magnesium intake and the metabolic syndrome: epidemiologic evidence to date. *J Cardiometab Syndr* 2006; 1:351-355.

(19) Dong J Y, Xun P, He K, Qin L Q. Magnesium Intake and Risk of Type 2 Diabetes: Meta-analysis of prospective cohort studies. *Diabetes Care* 2011; 34:2116-2122.

(20) Colditz G A, Manson J E, Stampfer M J, Rosner B, Willett W C, Speizer F E. Diet and risk of clinical diabetes in women. *Am J Clin Nutr* 1992; 55:1018-1023.

(21) Lopez-Ridaura R, Willett W C, Rimm E B et al. Magnesium intake and risk of type 2 diabetes in men and women. *Diabetes Care* 2004; 27:134-140.

(22) Larsson S C, Wolk A. Magnesium intake and risk of type 2 diabetes: a meta-analysis. *J Intern Med* 2007; 262:208-214.

(23) Schulze M B, Schulz M, Heidemann C, Schienkiewitz A, Hoffmann K, Boeing H. Fiber and magnesium intake and incidence of type 2 diabetes: a prospective study and meta-analysis. *Arch Intern Med* 2007; 167:956-965.

(24) Singh R B. Effect of dietary magnesium supplementation in the prevention of coronary heart disease and sudden cardiac death. *Magnes Trace Elem* 1990; 9:143-151.

(25) Al Delaimy W K, Rimm E B, Willett W C, Stampfer M J, Hu F B. Magnesium intake and risk of coronary heart disease among men. *J Am Coll Nutr* 2004; 23:63-70.

(26) Song Y, Manson J E, Cook N R, Albert C M, Buring J E, Liu S. Dietary magnesium intake and risk of cardiovascular disease among women. *Am J Cardiol* 2005; 96:1135-1141.

(27) Chiuve S E, Sun Q, Curhan G C et al. Dietary and plasma magnesium and risk of coronary heart disease among women. *J Am Heart Assoc* 2013;2:e000114.

(28) Larsson S C, Orsini N, Wolk A. Dietary magnesium intake and risk of stroke: a meta-analysis of prospective studies. *Am J Clin Nutr* 2012; 95:362-366.

(29) Dai Q, Shu X O, Deng X et al. Modifying effect of calcium/magnesium intake ratio and mortality: a population-based cohort study. *BMJ Open* 2013;3.

(30) Arnaud M J. Update on the assessment of magnesium status. *Br J Nutr* 2008;99 Suppl 3:S24-S36.

(31) Liebscher D H, Liebscher D E. About the misdiagnosis of magnesium deficiency. *J Am Coll Nutr* 2004; 23:730S-731S.

(32) Gitelman H J, WELT L G. Magnesium deficiency. *Annu Rev Med* 1969; 20:233-242.

(33) Franz K B. A functional biological marker is needed for diagnosing magnesium deficiency. *J Am Coll Nutr* 2004; 23:738S-741S.

(34) Ryu M S, Langkamp-Henken B, Chang S M, Shankar M N, Cousins R J. Genomic analysis, cytokine expression, and microRNA profiling reveal biomarkers of human dietary zinc depletion and homeostasis. *Proc Natl Acad Sci USA* 2011; 108:20970-20975.

(35) Bishop K S, Ferguson L R. The Interaction between Epigenetics, Nutrition and the Development of Cancer. *Nutrients* 2015; 7:922-947.

(36) Jin S G, Wu X, Li A X, Pfeifer G P. Genomic mapping of 5-hydroxymethylcytosine in the human brain. *Nucleic Acids Res* 2011; 39:5015-5024.

(37) Wester P O. Magnesium. *Am J Clin Nutr* 1987; 45:1305-1312.

(38) Saris N E, Mervaala E, Karppanen H, Khawaja J A, Lewenstam A. Magnesium. An update on physiological, clinical and analytical aspects. *Clin Chim Acta* 2000; 294:1-26.

(39) Hartwig A. Role of magnesium in genomic stability. *Mutat Res* 2001; 475:113-121.

(40) Gueux E, Azais-Braesco V, Bussiere L, Grolier P, Mazur A, Rayssiguier Y. Effect of magnesium deficiency on triacylglycerol-rich lipoprotein and tissue susceptibility to peroxidation in relation to vitamin E content. *Br J Nutr* 1995; 74:849-856.

(41) Hans C P, Chaudhary D P, Bansal D D. Effect of magnesium supplementation on oxidative stress in alloxanic diabetic rats. *Magnes Res* 2003; 16:13-19.

(42) Yu M, Hon G C, Szulwach K E et al. Base-resolution analysis of 5-hydroxymethylcytosine in the mammalian genome. *Cell* 2012; 149:1368-1380.

(43) Yu M, Hon G C, Szulwach K E et al. Tet-assisted bisulfite sequencing of 5-hydroxymethylcytosine. *Nat Protoc* 2012; 7:2159-2170.

(44) Nazor K L, Boland M J, Bibikova M et al. Application of a low cost array-based technique—TAB-Array—for quantifying and mapping both 5 mC and 5hmC at single base resolution in human pluripotent stem cells. *Genomics* 2014; 104:358-367.

(45) Ziegler D. Type 2 diabetes as an inflammatory cardiovascular disorder. *Curr Mol Med* 2005; 5:309-322.

(46) Dibaba D T, Xun P, He K. Dietary magnesium intake is inversely associated with serum C-reactive protein levels: meta-analysis and systematic review. *Eur J Clin Nutr* 2014.

(47) Elin R J. Assessment of magnesium status. *Clin Chem* 1987; 33:1965-1970.

(48) Wallach S. Availability of body magnesium during magnesium deficiency. *Magnesium* 1988; 7:262-270.

(49) Hoenderop J G, Bindels R J. Epithelial Ca2+ and Mg2+ channels in health and disease. *J Am Soc Nephrol* 2005; 16:15-26.

(50) Brown E M, Gamba G, Riccardi D et al. Cloning and characterization of an extracellular Ca(2+)-sensing receptor from bovine parathyroid. *Nature* 1993; 366:575-580.

(51) Brown E M, MacLeod R J. Extracellular calcium sensing and extracellular calcium signaling. *Physiol Rev* 2001; 81:239-297.

(52) Rude R K, Oldham S B, Sharp C F, Jr., Singer F R. Parathyroid hormone secretion in magnesium deficiency. *J Clin Endocrinol Metab* 1978; 47:800-806.

(53) Weaver C M. Assessing calcium status and metabolism. *J Nutr* 1990;120 Suppl 11:1470-1473.

(54) Arnold A, Tovey J, Mangat P, Penny W, Jacobs S. Magnesium deficiency in critically ill patients. *Anaesthesia* 1995; 50:203-205.

(55) Ryzen E, Elkayam U, Rude R K. Low blood mononuclear cell magnesium in intensive cardiac care unit patients. *Am Heart J* 1986; 111:475-480.

(56) Ryzen E, Elbaum N, Singer F R, Rude R K. Parenteral magnesium tolerance testing in the evaluation of magnesium deficiency. *Magnesium* 1985; 4:137-147.

(57) Lukaski H C, Nielsen F H. Dietary magnesium depletion affects metabolic responses during submaximal exercise in postmenopausal women. *J Nutr* 2002; 132:930-935.

(58) Akarolo-Anthony S N, Jimenez M C, Chiuve S E, Spiegelman D, Willett W C, Rexrode K M. Plasma magnesium and risk of ischemic stroke among women. *Stroke* 2014; 45:2881-2886.

(59) Gullestad L, Oystein D L, Birkeland K, Falch D, Fagertun H, Kjekshus J. Oral versus intravenous magnesium supplementation in patients with magnesium deficiency. *Magnes Trace Elem* 1991; 10:11-16.

(60) Duckworth J, Godden W. The influence of diets low in magnesium upon the chemical composition of the incisor tooth of the rat. *J Physiol* 1940; 99:1-7.

(61) Chaudhary D P, Sharma R, Bansal D D. Implications of magnesium deficiency in type 2 diabetes: a review. *Biol Trace Elem Res* 2010; 134:119-129.

(62) Khan A M, Lubitz S A, Sullivan L M et al. Low serum magnesium and the development of atrial fibrillation in the community: the *Framingham Heart Study. Circulation* 2013; 127:33-38.

(63) Peacock J M, Ohira T, Post W, Sotoodehnia N, Rosamond W, Folsom A R. Serum magnesium and risk of sudden cardiac death in the Atherosclerosis Risk in Communities (ARIC) Study. *Am Heart J* 2010; 160:464-470.

(64) Rude R K, Gruber H E, Norton H J, Wei L Y, Frausto A, Kilburn J. Reduction of dietary magnesium by only 50% in the rat disrupts bone and mineral metabolism. *Osteoporos Int* 2006; 17:1022-1032.

(65) Wu L, Luthringer B J, Feyerabend F, Schilling A F, Willumeit R. Effects of extracellular magnesium on the differentiation and function of human osteoclasts. *Acta Biomater* 2014.

(66) Belluci M M, Schoenmaker T, Rossa-Junior C, Orrico S R, de Vries T J, Everts V. Magnesium deficiency results in an increased formation of osteoclasts. *JN utr Biochem* 2013; 24:1488-1498.

(67) Kuzmac S, Grcevic D, Sucur A, Ivcevic S, Katavic V. Acute hematopoietic stress in mice is followed by enhanced osteoclast maturation in the bone marrow microenvironment. *Exp Hematol* 2014; 42:966-975.

(68) Bestor T H, Tycko B. Creation of genomic methylation patterns. *Nat Genet* 1996; 12:363-367.

(69) Jimenez-Useche I, Yuan C. The effect of DNA CpG methylation on the dynamic conformation of a nucleosome. *Biophys J* 2012; 103:2502-2512.

(70) Lu X, Zhao B S, He C. TET Family Proteins: Oxidation Activity, Interacting Molecules, and Functions in Diseases. *Chem Rev* 2015.

(71) Kriaucionis S, Heintz N. The nuclear DNA base 5-hydroxymethylcytosine is present in Purkinje neurons and the brain. *Science* 2009; 324:929-930.

(72) Tahiliani M, Koh K P, Shen Y et al. Conversion of 5-methylcytosine to 5-hydroxymethylcytosine in mammalian DNA by MLL partner TET1. *Science* 2009; 324:930-935.

(73) Branco M R, Ficz G, Reik W. Uncovering the role of 5-hydroxymethylcytosine in the epigenome. *Nat Rev Genet* 2012; 13:7-13.

(74) Wu H, Zhang Y. Mechanisms and functions of Tet protein-mediated 5-methylcytosine oxidation. *Genes Dev* 2011; 25:2436-2452.

(75) He Y F, Li B Z, Li Z et al. Tet-mediated formation of 5-carboxylcytosine and its excision by TDG in mammalian DNA. *Science* 2011; 333:1303-1307.

(76) Ito S, Shen L, Dai Q et al. Tet proteins can convert 5-methylcytosine to 5-formylcytosine and 5-carboxylcytosine. *Science* 2011; 333:1300-1303.

(77) Bhutani N, Burns D M, Blau H M. DNA demethylation dynamics. *Cell* 2011; 146:866-872.

(78) Globisch D, Munzel M, Muller M et al. Tissue distribution of 5-hydroxymethylcytosine and search for active demethylation intermediates. *PLoS One* 2010;5:e15367.

(79) Pfaffeneder T, Hackner B, Truss M et al. The discovery of 5-formylcytosine in embryonic stem cell DNA. *Angew Chem Int Ed Engl* 2011; 50:7008-7012.

(80) Robertson K D, Wolffe A P. DNA methylation in health and disease. *Nat Rev Genet* 2000; 1:11-19.

(81) Dunn B K. Hypomethylation: one side of a larger picture. *Ann NY Acad Sci* 2003; 983:28-42.

(82) Mariani C J, Madzo J, Moen E L, Yesilkanal A, Godley L A. Alterations of 5-hydroxymethylcytosine in human cancers. *Cancers (Basel)* 2013; 5:786-814.

(83) Bibikova M, Barnes B, Tsan C et al. High density DNA methylation array with single CpG site resolution. *Genomics* 2011; 98:288-295.

(84) Mithieux G, Vega F V, Riou J P. The liver glucose-6-phosphatase of intact microsomes is inhibited and displays sigmoid kinetics in the presence of alpha-ketoglutarate-magnesium and oxaloacetate-magnesium chelates. *J Biol Chem* 1990; 265:20364-20368.

(85) Panov A, Scarpa A. Independent modulation of the activity of alpha-ketoglutarate dehydrogenase complex by $Ca^{2+}$ and $Mg^{2+}$. *Biochemistry* 1996; 35:427-432.

(86) Blaschke K, Ebata K T, Karimi M M et al. Vitamin C induces Tet-dependent DNA demethylation and a blastocyst-like state in E S cells. *Nature* 2013; 500:222-226.

(87) Yin R, Mao S Q, Zhao B et al. Ascorbic acid enhances Tet-mediated 5-methylcytosine oxidation and promotes DNA demethylation in mammals. *J Am Chem Soc* 2013; 135:10396-10403.

(88) Graves T L, Zhang Y, Scott J E. A universal competitive fluorescence polarization activity assay for S-adenosylmethionine utilizing methyltransferases. *Anal Biochem* 2008; 373:296-306.

(89) Hoffman D R, Cornatzer W E, Duerre J A. Relationship between tissue levels of S-adenosylmethionine, S-adenylhomocysteine, and transmethylation reactions. *Can J Biochem* 1979; 57:56-65.

(90) Kerr S J, Heady J E. Modulation of tRNA methyltransferase activity by competing enzyme systems. *Adv Enzyme Regul* 1974; 12:103-117.

(91) Castro R, Rivera I, Struys E A et al. Increased homocysteine and S-adenosylhomocysteine concentrations and DNA hypomethylation in vascular disease. *Clin Chem* 2003; 49:1292-1296.

(92) Yi P, Melnyk S, Pogribna M, Pogribny I P, Hine R J, James S J. Increase in plasma homocysteine associated with parallel increases in plasma S-adenosylhomocysteine and lymphocyte DNA hypomethylation. *J Biol Chem* 2000; 275:29318-29323.

(93) Zhang B, Denomme M M, White C R et al. Both the folate cycle and betaine-homocysteine methyltransferase contribute methyl groups for DNA methylation in mouse blastocysts. *FASEB J* 2015; 29:1069-1079.

(94) Pfalzer A C, Choi S W, Tammen S A et al. S-adenosylmethionine mediates inhibition of inflammatory response and changes in DNA methylation in human macrophages. *Physiol Genomics* 2014; 46:617-623.

(95) Inoue-Choi M, Nelson H H, Robien K et al. Plasma S-adenosylmethionine, DNMT polymorphisms, and peripheral blood LINE-1 methylation among healthy Chinese adults in Singapore. *BMC Cancer* 2013; 13:389.

(96) Caudill M A, Wang J C, Melnyk S et al. Intracellular S-adenosylhomocysteine concentrations predict global DNA hypomethylation in tissues of methyl-deficient cystathionine beta-synthase heterozygous mice. *J Nutr* 2001; 131:2811-2818.

(97) Da M X, Zhang Y B, Yao J B, Duan Y X. DNA methylation regulates expression of VEGF-C, and S-adenosylmethionine is effective for VEGF-C methylation and for inhibiting cancer growth. *Braz J Med Biol Res* 2014; 47:1021-1028.

(98) Wasson G R, McGlynn A P, McNulty H et al. Global DNA and p53 region-specific hypomethylation in human colonic cells is induced by folate depletion and reversed by folate supplementation. *J Nutr* 2006; 136:2748-2753.

(99) Jacob R A, Gretz D M, Taylor P C et al. Moderate folate depletion increases plasma homocysteine and decreases lymphocyte DNA methylation in postmenopausal women. *J Nutr* 1998; 128:1204-1212.

(100) Rampersaud G C, Kauwell G P, Hutson A D, Cerda J J, Bailey L B. Genomic DNA methylation decreases in response to moderate folate depletion in elderly women. *Am J Clin Nutr* 2000; 72:998-1003.

(101) Basten G P, Duthie S J, Pirie L, Vaughan N, Hill M H, Powers H J. Sensitivity of markers of DNA stability and DNA repair activity to folate supplementation in healthy volunteers. *Br J Cancer* 2006; 94:1942-1947.

(102) Fenech M, Aitken C, Rinaldi J. Folate, vitamin B12, homocysteine status and DNA damage in young Australian adults. *Carcinogenesis* 1998; 19:1163-1171.

(103) Ingrosso D, Cimmino A, Perna A F et al. Folate treatment and unbalanced methylation and changes of allelic expression induced by hyperhomocysteinemia in patients with uraemia. *Lancet* 2003; 361:1693-1699.

(104) Pufulete M, Al-Ghnaniem R, Khushal A et al. Effect of folic acid supplementation on genomic DNA methylation in patients with colorectal adenoma. *Gut* 2005; 54:648-653.

(105) Gao F, Xia Y, Wang J et al. Integrated detection of both 5-mC and 5-hmC by high-throughput tag sequencing technology highlights methylation reprogramming of bivalent genes during cellular differentiation. *Epigenetics* 2013; 8:421-430.

(106) Imperiale T F, Ransohoff D F, Itzkowitz S H et al. Multitarget stool DNA testing for colorectal-cancer screening. *N Engl J Med* 2014; 370:1287-1297.

(107) Kao W H, Folsom A R, Nieto F J, Mo J P, Watson R L, Brancati F L. Serum and dietary magnesium and the risk for type 2 diabetes mellitus: the Atherosclerosis Risk in Communities Study. *Arch Intern Med* 1999; 159:2151-2159.

(108) Everett C J, King D E. Serum magnesium and the development of diabetes. *Nutrition* 2006; 22:679.

(109) Liao F, Folsom A R, Brancati F L. Is low magnesium concentration a risk factor for coronary heart disease? The Atherosclerosis Risk in Communities (ARIC) Study. *Am Heart J* 1998; 136:480-490.

(110) Ford E S, Bowman B A. Serum and red blood cell folate concentrations, race, and education: findings from the third National Health and Nutrition Examination Survey. *Am J Clin Nutr* 1999; 69:476-481.

(111) Khan A M, Sullivan L, McCabe E, Levy D, Vasan R S, Wang T J. Lack of association between serum magnesium and the risks of hypertension and cardiovascular disease. *Am Heart J* 2010; 160:715-720.

(112) Joosten M M, Gansevoort R T, Mukamal K J et al. Urinary and plasma magnesium and risk of ischemic heart disease. *Am J Clin Nutr* 2013.

(113) Ohira T, Peacock J M, Iso H, Chambless L E, Rosamond W D, Folsom A R. Serum and dietary magnesium and risk of ischemic stroke: the Atherosclerosis Risk in Communities Study. *Am J Epidemiol* 2009; 169:1437-1444.

(114) Domrongkitchaiporn S, Ongphiphadhanakul B, Stitchantrakul W et al. Risk of calcium oxalate nephrolithiasis after calcium or combined calcium and calcitriol supplementation in postmenopausal women. *Osteoporos Int* 2000; 11:486-492.

(115) Norman D A, Fordtran J S, Brinkley L J et al. Jejunal and ileal adaptation to alterations in dietary calcium: changes in calcium and magnesium absorption and pathogenetic role of parathyroid hormone and 1,25-dihydroxyvitamin D. *J Clin Invest* 1981; 67:1599-1603.

(116) Hardwick L L, Jones M R, Brautbar N, Lee D B. Magnesium absorption: mechanisms and the influence of vitamin D, calcium and phosphate. *J Nutr* 1991; 121:13-23.

(117) Green J H, Booth C, Bunning R. Acute effect of high-calcium milk with or without additional magnesium, or calcium phosphate on parathyroid hormone and biochemical markers of bone resorption. *Eur J Clin Nutr* 2003; 57:61-68.

(118) Nielsen F H, Milne D B, Gallagher S, Johnson L, Hoverson B. Moderate magnesium deprivation results in calcium retention and altered potassium and phosphorus excretion by postmenopausal women. *Magnes Res* 2007; 20:19-31.

(119) Karkkainen M U, Wiersma J W, Lamberg-Allardt C J. Postprandial parathyroid hormone response to four calcium-rich foodstuffs. *Am J Clin Nutr* 1997; 65:1726-1730.

(120) Abbott L, Nadler J, Rude R K. Magnesium deficiency in alcoholism: possible contribution to osteoporosis and cardiovascular disease in alcoholics. *Alcohol Clin Exp Res* 1994; 18:1076-1082.

(121) Poikolainen K, Alho H. Magnesium treatment in alcoholics: a randomized clinical trial. *Subst Abuse Treat Prev Policy* 2008; 3:1.

(122) Resnick L M, Altura B T, Gupta R K, Laragh J H, Alderman M H, Altura B M. Intracellular and extracellular magnesium depletion in type 2 (non-insulin-dependent) diabetes mellitus. *Diabetologia* 1993; 36:767-770.

(123) Alexandropoulou K, van V J, Reid F, Poullis A, Kang J Y. Temporal trends of Barrett's oesophagus and gastro-oesophageal reflux and related oesophageal cancer over a 10-year period in England and Wales and associated proton pump inhibitor and H2R A prescriptions: a GPRD study. *Eur J Gastroenterol Hepatol* 2013; 25:15-21.

(124) Bai J P, Hausman E, Lionberger R, Zhang X. Modeling and simulation of the effect of proton pump inhibitors on magnesium homeostasis. 1. Oral absorption of magnesium. *Mol Pharm* 2012; 9:3495-3505.

(125) Luk C P, Parsons R, Lee Y P, Hughes J D. Proton pump inhibitor-associated hypomagnesemia: what do FDA data tell us?*Ann Pharmacother* 2013; 47:773-780.

(126) Markovits N, Loebstein R, Halkin H et al. The association of proton pump inhibitors and hypomagnesemia in the community setting. *J Clin Pharmacol* 2014; 54:889-895.

(127) Pak C Y. Correction of thiazide-induced hypomagnesemia by potassium-magnesium citrate from review of prior trials. *Clin Nephrol* 2000; 54:271-275.

(128) Oka T, Kimura T, Suzumura T et al. Magnesium supplementation and high volume hydration reduce the renal toxicity caused by cisplatin-based chemotherapy in patients with lung cancer: a toxicity study. *BMC Pharmacol Toxicol* 2014; 15:70.

(129) Schrag D, Chung K Y, Flombaum C, Saltz L. Cetuximab therapy and symptomatic hypomagnesemia. *J Natl Cancer Inst* 2005; 97:1221-1224.

(130) Haenni A, Ohrvall M, Lithell H. Serum magnesium status during lipid-lowering drug treatment in non-insulin-dependent diabetic patients. *Metabolism* 2001; 50:1147-1151.

(131) Meyer T E, Verwoert G C, Hwang S J et al. Genome-wide association studies of serum magnesium, potassium, and sodium concentrations identify six Loci influencing serum magnesium levels. *PLoS Genet* 2010;6.

(132) Schmitz C, Perraud A L, Johnson C O et al. Regulation of vertebrate cellular Mg2+ homeostasis by TRPM7. *Cell* 2003; 114:191-200.

(133) Baastrup R, Sorensen M, Balstrom T et al. Arsenic in drinking-water and risk for cancer in Denmark. *Environ Health Perspect* 2008; 116:231-237.

(134) Hou L, Ji B T, Blair A et al. Body mass index and colon cancer risk in Chinese people: menopause as an effect modifier. *Eur J Cancer* 2006; 42:84-90.

(135) Hou L, Ji B T, Blair A, Dai Q, Gao Y T, Chow W H. Commuting physical activity and risk of colon cancer in Shanghai, China. *Am J Epidemiol* 2004; 160:860-867.

(136) Shrubsole M J, Wagner C, Zhu X et al. Associations between S-adenosylmethionine, S-adenosylhomocysteine, and colorectal adenoma risk are modified by sex. *Am J Cancer Res* 2015; 5:458-465.

(137) Wang L, Zhang J, Duan J et al. Programming and inheritance of parental DNA methylomes in mammals. *Cell* 2014; 157:979-991.

(138) Lister R, Mukamel E A, Nery J R et al. Global epigenomic reconfiguration during mammalian brain development. *Science* 2013; 341:1237905.

(139) Ito S, Shen L, Dai Q et al. Tet proteins can convert 5-methylcytosine to 5-formylcytosine and 5-carboxylcytosine. *Science* 2011; 333:1300-1303.

(140) Szulwach K E, Li X, Li Y et al. 5-hmC-mediated epigenetic dynamics during postnatal neurodevelopment and aging. *Nat Neurosci* 2011; 14:1607-1616.

(141) Song C X, Yi C, He C. Mapping recently identified nucleotide variants in the genome and transcriptome. *Nat Biotechnol* 2012; 30:1107-1116.

(142) Song C X, Szulwach K E, Fu Y et al. Selective chemical labeling reveals the genome-wide distribution of 5-hydroxymethylcytosine. *Nat Biotechnol* 2011; 29:68-72.

(143) Song C X, Clark T A, Lu X Y et al. Sensitive and specific single-molecule sequencing of 5-hydroxymethylcytosine. *Nat Methods* 2012; 9:75-77.

(144) Kellinger M W, Song C X, Chong J, Lu X Y, He C, Wang D. 5-formylcytosine and 5-carboxylcytosine reduce the rate and substrate specificity of RNA polymerase II transcription. *Nat Struct Mol Biol* 2012; 19:831-833.

(145) Hon G C, Song C X, Du T et al. 5 mC oxidation by Tet2 modulates enhancer activity and timing of transcriptome reprogramming during differentiation. *Mol Cell* 2014; 56:286-297.

(146) Huang H, Jiang X, Li Z et al. TET1 plays an essential oncogenic role in MLL-rearranged leukemia. *Proc Natl Acad Sci USA* 2013; 110:11994-11999.

(147) He Y F, Li B Z, Li Z et al. Tet-mediated formation of 5-carboxylcytosine and its excision by TDG in mammalian DNA. *Science* 2011; 333:1303-1307.

(148) Gan H, Wen L, Liao S et al. Dynamics of 5-hydroxymethylcytosine during mouse spermatogenesis. *Nat Commun* 2013; 4:1995.

(149) Flatman P W. Mechanisms of magnesium transport. *Annu Rev Physiol* 1991; 53:259-271.

(150) Bind M A, Lepeule J, Zanobetti A et al. Air pollution and gene-specific methylation in the Normative Aging Study: association, effect modification, and mediation analysis. *Epigenetics* 2014; 9:448-458.

(151) Zhu Z Z, Sparrow D, Hou L et al. Repetitive element hypomethylation in blood leukocyte DNA and cancer incidence, prevalence, and mortality in elderly individuals: the Normative Aging Study. *Cancer Causes Control* 2011; 22:437-447.

(152) van de Rest O, Spiro A, III, Krall-Kaye E, Geleijnse J M, de Groot L C, Tucker K L. Intakes of (n-3) fatty acids and fatty fish are not associated with cognitive performance and 6-year cognitive change in men participating in the Veterans Affairs Normative Aging Study. *J Nutr* 2009; 139:2329-2336.

(153) Langmead B, Salzberg S L. Fast gapped-read alignment with Bowtie 2. *Nat Methods* 2012; 9:357-359.

(154) Feng J, Liu T, Qin B, Zhang Y, Liu X S. Identifying ChIP-seq enrichment using MACS. *Nat Protoc* 2012; 7:1728-1740.

(155) Huang d W, Sherman B T, Lempicki R A. Systematic and integrative analysis of large gene lists using DAVID bioinformatics resources. *Nat Protoc* 2009; 4:44-57.

(156) Baccarelli A A, Zheng Y, Zhang X et al. Air pollution exposure and lung function in highly exposed subjects in Beijing, China: a repeated-measure study. *Part Fibre Toxicol* 2014; 11:51.

(157) Hou L, Zhang X, Zheng Y et al. Altered methylation in tandem repeat element and elemental component levels in inhalable air particles. *Environ Mol Mutagen* 2014; 55:256-265.

(158) Hou L, Zhang X, Dioni L et al. Inhalable particulate matter and mitochondrial DNA copy number in highly exposed individuals in Beijing, China: a repeated-measure study. *Part Fibre Toxicol* 2013; 10:17.

(159) Dai Q, Shrubsole M J, Ness R M et al. The relation of magnesium and calcium intakes and a genetic polymorphism in the magnesium transporter to colorectal neoplasia risk. *Am J Clin Nutr* 2007; 86:743-751.

(160) Dai Q, Sandler R, Barry E, Summers R, Grau M, Baron J. Calcium, magnesium, and colorectal cancer. *Epidemiology* 2012; 23:504-505.

(161) Sahota O, Mundey M K, San P, Godber I M, Hosking D J. Vitamin D insufficiency and the blunted PTH response in established osteoporosis: the role of magnesium deficiency. *Osteoporos Int* 2006; 17:1013-1021.
(162) Butler L M, Arning E, Wang R et al. Prediagnostic levels of serum one-carbon metabolites and risk of hepatocellular carcinoma. *Cancer Epidemiol Biomarkers Prev* 2013; 22:1884-1893.
(163) Ducros V, Belva-Besnet H, Casetta B, Favier A. A robust liquid chromatography tandem mass spectrometry method for total plasma homocysteine determination in clinical practice. *Clin Chem Lab Med* 2006; 44:987-990.
(164) Poirier L A, Wise C K, Delongchamp R R, Sinha R. Blood determinations of S-adenosylmethionine, S-adenosylhomocysteine, and homocysteine: correlations with diet. *Cancer Epidemiol Biomarkers Prev* 2001; 10:649-655.
(165) Dai Q, Motley S S, Smith J A, Jr. et al. Blood magnesium, and the interaction with calcium, on the risk of high-grade prostate cancer. *PLoS One* 2011;6:e18237.
(166) Du P, Zhang X, Huang C C et al. Comparison of Beta-value and M-value methods for quantifying methylation levels by microarray analysis. *BMC Bioinformatics* 2010; 11:587.
(167) Zhang X, Mu W, Zhang W. On the analysis of the illumina 450 k array data: probes ambiguously mapped to the human genome. *Front Genet* 2012; 3:73.
(168) Moen E L, Zhang X, Mu W et al. Genome-wide variation of cytosine modifications between European and African populations and the implications for complex traits. *Genetics* 2013; 194:987-996.
(169) He C, Jiang H, Geng S et al. Analysis of whole genomic expression profiles and screening of the key signaling pathways associated with pancreatic cancer. *Int J Clin Exp Pathol* 2012; 5:537-546.
(170) Li D, Duell E J, Yu K et al. Pathway analysis of genome-wide association study data highlights pancreatic development genes as susceptibility factors for pancreatic cancer. *Carcinogenesis* 2012; 33:1384-1390.
(171) Wu C, Miao X, Huang L et al. Genome-wide association study identifies five loci associated with susceptibility to pancreatic cancer in Chinese populations. *Nat Genet* 2012; 44:62-66.
(172) Benjamini Y, Hochberg Y. Controlling the false discovery rate: A practical and powerful approach to multiple testing. *Journal of the Royal Statistical Society* 1995; 289-300.
(173) Harrell F E. Regression Modeling Strategies: *With Applications to Linear Models, Logistic Regression, and Survival Analysis*. New York: Springer, 2001.
(174) Steyerberg E W. Clinical Prediction Models—A practical approach to development, validation, and updating. 2009. New York, Springer. Ref Type: Serial (Book, Monograph)
(175) Su Y, Shrubsole M J, Ness R M et al. Immunohistochemical expressions of Ki-67, cyclin D1, beta-catenin, cyclooxygenase-2, and epidermal growth factor receptor in human colorectal adenoma: a validation study of tissue microarrays. *Cancer Epidemiol Biomarkers Prev* 2006; 15:1719-1726.
(176) Su Y, Shrubsole M, Rex D K et al. Biomarker expression in proximal and distal colorectal adenomas. [abstract] Su Y, Shrubsole M, Rex D K et al. *AACR meeting* 2008;
(177) Yee N S, Kazi A A, Yee R K. Cellular and Developmental Biology of TRPM7 Channel-Kinase: Implicated Roles in Cancer. *Cells* 2014; 3:751-777.
(178) Mohania D, Kansal V K, Kruzliak P, Kumari A. Probiotic Dahi containing *Lactobacillus acidophilus* and *Bifidobacterium bifidum* modulates the formation of aberrant crypt foci, mucin-depleted foci, and cell proliferation on 1,2-dimethylhydrazine-induced colorectal carcinogenesis in Wistar rats. *Rejuvenation Res* 2014; 17:325-333.
(179) Thun M J, Henley S J, Patrono C. Nonsteroidal anti-inflammatory drugs as anticancer agents: mechanistic, pharmacologic, and clinical issues. *J Natl Cancer Inst* 2002; 94:252-266.
(180) Chan T A. Nonsteroidal anti-inflammatory drugs, apoptosis, and colon-cancer chemoprevention. *Lancet Oncol* 2002; 3:166-174.
(181) Chan P, Cheng J T, Tsai J C et al. Effect of catechin on the activity and gene expression of superoxide dismutase in cultured rat brain astrocytes. *Neurosci Lett* 2002; 328:281-284.
(182) Baron J A. Epidemiology of non-steroidal anti-inflammatory drugs and cancer. *Prog Exp Tumor Res* 2003; 37:1-24.
(183) Baron J A, Cole B F, Sandler R S et al. A randomized trial of aspirin to prevent colorectal adenomas. *N Engl J Med* 2003; 348:891-899.
(184) Giardiello F M, Hamilton S R, Krush A J et al. Treatment of colonic and rectal adenomas with sulindac in familial adenomatous polyposis. *N Engl J Med* 1993; 328:1313-1316.
(185) Steinbach G, Lynch P M, Phillips R K et al. The effect of celecoxib, a cyclooxygenase-2 inhibitor, in familial adenomatous polyposis. *N Engl J Med* 2000; 342:1946-1952.
(186) Brown J R, DuBois R N. COX-2: a molecular target for colorectal cancer prevention. *J Clin Oncol* 2005; 23:2840-2855.
(187) Bedi A, Pasricha P J, Akhtar A J et al. Inhibition of apoptosis during development of colorectal cancer. *Cancer Res* 1995; 55:1811-1816.
(188) Tibshirani R (1996). Regression shrinkage and selection via the lasso. *Journal of the Royal Statistical Society* B 58: 267-288.
(189) Zou H, Hastie T (2005). Regularization and variable selection via the elastic net. *Journal of the Royal Statistical Society* B 57: 301-320.
(190) Harrell Jr. F E (2015) Regression Modeling Strategies: With Applications to Linear Models, Logistic and Ordinal Regression, and Survival Analysis, 2nd edition, Springer Series in Statistics.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for predicting and treating magnesium deficiency in a subject, said method comprising:
   a) detecting methylation at CpG sites in DNA obtained from a biological sample from the subject, wherein the subject is in need of assessment for magnesium deficiency status; and
   b) identifying the subject as being in need of magnesium supplementation when methylation is found at the CpG site: cg00430271 or cg25731074; and
   c) administering an effective amount of magnesium to the identified subject.

2. The method of claim 1, and further comprising detecting 5-hydroxymethylcytosine (5-hmC) and 5-methylcytosine (5-mC) methylation in the DNA obtained from the biological sample from the subject and differentiating between 5-hmC and 5-mC methylation in the sample.

3. The method of claim 1, further comprising detecting 5-hmC and 5-mC methylation, 5-hmC methylation, or 5-mC methylation by performing bisulfite (BS) treatment of the DNA in the biological sample.

4. The method of claim 2, further comprising differentiating between 5-hmC and 5-mC methylation in the biological sample using a TAB-Seq and TAB-Array protocol.

5. The method of claim 1, and further comprising determining for the subject a magnesium tolerance test (MTT) score, where an MTT score of greater than or equal to 50% is further indicative of a magnesium deficiency, an MTT score of less than 50% and greater than or equal to 25% is further indicative of a magnesium insufficiency, and an MTT score of less than 25% is further indicative of a magnesium sufficiency.

6. The method of claim 1, and further comprising identifying the subject as being in need of magnesium supplementation when methylation is found at the CpG sites comprising: cg00430271 and cg25731074.

7. The method of claim 6, and further comprising administering an effective amount of magnesium to the identified subject.

8. The method of claim 1, wherein the biological sample includes blood leukocyte DNA.

9. The method of claim 1, and further comprising identifying the subject as being in need of magnesium supplementation when methylation is found at the CpG sites comprising: cg00430271, cg11840205, and cg25731074.

10. The method of claim 9, and further comprising administering an effective amount of magnesium to the identified subject.

11. The method of claim 1, and further comprising identifying the subject as being in need of magnesium supplementation when methylation is found at the CpG sites comprising: cg00430271, cg04386563, cg11840205, and cg25731074.

12. The method of claim 11, and further comprising administering an effective amount of magnesium to the identified subject.

13. The method of claim 1, and further comprising determining Ca:Mg ratio of the diet of the subject, and selecting the effective amount of magnesium to decrease the Ca:Mg ratio.

* * * * *